(12) United States Patent
Yamamoto et al.

(10) Patent No.: US 11,944,703 B2
(45) Date of Patent: *Apr. 2, 2024

(54) OCULAR INJECTOR AND METHODS FOR ACCESSING SUPRACHOROIDAL SPACE OF THE EYE

(71) Applicant: Clearside Biomedical, Inc., Alpharetta, GA (US)

(72) Inventors: Ronald Yamamoto, San Francisco, CA (US); Stanley R. Conston, San Carlos, CA (US); David Sierra, Aptos, CA (US)

(73) Assignee: Clearside Biomedical, Inc., Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/365,024

(22) Filed: Aug. 3, 2023

(65) Prior Publication Data

US 2023/0372235 A1 Nov. 23, 2023

Related U.S. Application Data

(63) Continuation of application No. 17/711,495, filed on Apr. 1, 2022, now Pat. No. 11,752,101, which is a (Continued)

(51) Int. Cl.
*A61F 9/007* (2006.01)
*A61F 9/00* (2006.01)
(Continued)

(52) U.S. Cl.
CPC .......... *A61K 9/0048* (2013.01); *A61F 9/0017* (2013.01); *A61F 9/0026* (2013.01);
(Continued)

(58) Field of Classification Search
CPC .. A61F 9/00739; A61F 9/0008; A61F 9/0017; A61F 9/0026; A61F 9/007;
(Continued)

(56) References Cited

U.S. PATENT DOCUMENTS 1,527,291 A 2/1925 Guillermo et al.
2,187,259 A 1/1940 Barnhart
(Continued)

FOREIGN PATENT DOCUMENTS

CA 2639322 A1 3/2009
CN 1229679 A 9/1999
(Continued)

OTHER PUBLICATIONS

Abbott Laboratories Inc., Abbott Park, Illinois, USA, Abbott Medical Optics, "HEALON5 OVD," 2004, [online]. Retrieved from the Interent: URL: http://abbottmedicaloptics.com/products/cataract/ovds/healon5-viscoelastic. Retrieved from the Internet on: Aug. 16, 2016, 5 pages.

(Continued)

*Primary Examiner* — Robert J Utama
*Assistant Examiner* — Leah J Swanson
(74) *Attorney, Agent, or Firm* — COOLEY LLP

(57) ABSTRACT

An ocular medical injector is provided for drug delivery. A method includes inserting a puncture member of the medical injector into the eye until the puncture member reaches the suprachoroidal space (SCS). The puncture member defines a lumen therethrough. With the puncture member disposed within the SCS, a flexible cannula is advanced distally through the lumen of the puncture member, beyond the distal end portion of the puncture member and along the SCS towards a posterior region of the eye. The flexible cannula has an atraumatic distal tip and defines a lumen therethrough. With the distal tip of the flexible cannula disposed (Continued)

within the SCS beyond a distal end portion of the puncture member, a therapeutic substance is administered to the SCS.

22 Claims, 6 Drawing Sheets

Related U.S. Application Data continuation of application No. 17/217,455, filed on Mar. 30, 2021, now abandoned, which is a continuation of application No. 16/741,473, filed on Jan. 13, 2020, now abandoned, which is a continuation of application No. 11/709,941, filed on Feb. 21, 2007, now abandoned.

(60) Provisional application No. 60/776,903, filed on Feb. 22, 2006.

(51) Int. Cl.
    *A61K 9/00*     (2006.01)
    *A61K 9/16*     (2006.01)
    *A61K 31/717*     (2006.01)
    *A61K 31/718*     (2006.01)
    *A61K 31/722*     (2006.01)
    *A61K 31/728*     (2006.01)
    *A61K 31/737*     (2006.01)
    *A61K 47/36*     (2006.01)
    *A61M 5/31*     (2006.01)
    *A61M 5/48*     (2006.01)
    *A61K 9/14*     (2006.01)

(52) U.S. Cl.
    CPC .......... *A61F 9/007* (2013.01); *A61F 9/00736* (2013.01); *A61K 9/0051* (2013.01); *A61K 9/1635* (2013.01); *A61K 31/717* (2013.01); *A61K 31/718* (2013.01); *A61K 31/722* (2013.01); *A61K 31/728* (2013.01); *A61K 31/737* (2013.01); *A61K 47/36* (2013.01); *A61M 5/486* (2013.01); *A61K 9/14* (2013.01); *A61M 2005/3103* (2013.01); *A61M 2210/0612* (2013.01)

(58) Field of Classification Search
    CPC ............... A61F 9/00736; A61M 5/486; A61M 2005/3103; A61M 2210/0612; A61K 9/0048; A61K 9/0051; A61K 9/14; A61K 9/1635; A61K 31/717; A61K 31/718; A61K 31/722; A61K 31/728; A61K 31/737; A61K 47/36; A61K 9/50; A61K 31/716; A61K 38/39
    See application file for complete search history.

(56) References Cited

U.S. PATENT DOCUMENTS

| | | |
|---|---|---|
| 2,623,521 A | 12/1952 | Shaw |
| 2,841,145 A | 7/1958 | Epps |
| 2,939,459 A | 6/1960 | Lazarte et al. |
| 3,376,999 A | 4/1968 | De et al. |
| 3,477,432 A | 11/1969 | Shaw et al. |
| 3,739,947 A | 6/1973 | Baumann et al. |
| 3,762,540 A | 10/1973 | Baumann et al. |
| 3,788,320 A | 1/1974 | Dye |
| 3,838,690 A | 10/1974 | Friedman |
| 3,892,311 A | 7/1975 | Sneider |
| 3,962,430 A | 6/1976 | O'Neill |
| 3,964,482 A | 6/1976 | Gerstel et al. |
| 4,226,328 A | 10/1980 | Beddow |
| 4,230,112 A | 10/1980 | Smith |
| 4,303,071 A | 12/1981 | Smith |
| 4,317,448 A | 3/1982 | Smith |
| 4,377,897 A | 3/1983 | Eichenbaum et al. |
| 4,383,530 A | 5/1983 | Bruno |
| 4,417,887 A | 11/1983 | Koshi |
| 4,432,964 A | 2/1984 | Shell et al. |
| 4,501,363 A | 2/1985 | Isbey, Jr. |
| 4,525,346 A | 6/1985 | Stark |
| 4,564,016 A | 1/1986 | Maurice et al. |
| 4,573,993 A | 3/1986 | Hoag et al. |
| 4,601,708 A | 7/1986 | Jordan |
| 4,615,331 A | 10/1986 | Kramann |
| 4,627,841 A | 12/1986 | Dorr |
| 4,662,870 A | 5/1987 | Augustine et al. |
| 4,662,878 A | 5/1987 | Lindmayer |
| 4,689,040 A | 8/1987 | Thompson |
| 4,708,147 A | 11/1987 | Haaga |
| 4,717,383 A | 1/1988 | Phillips et al. |
| 4,736,850 A | 4/1988 | Bowman et al. |
| 4,755,169 A | 7/1988 | Sarnoff et al. |
| 4,795,432 A | 1/1989 | Karczmer |
| 4,804,371 A | 2/1989 | Vaillancourt |
| 4,826,490 A | 5/1989 | Byrne et al. |
| 4,826,871 A | 5/1989 | Gressel et al. |
| 4,883,483 A | 11/1989 | Lindmayer |
| 4,889,529 A | 12/1989 | Haindl |
| 4,941,874 A | 7/1990 | Sandow et al. |
| 4,966,773 A | 10/1990 | Gressel et al. |
| 5,015,240 A | 5/1991 | Soproni et al. |
| 5,023,087 A | 6/1991 | Yau-Young |
| 5,024,662 A | 6/1991 | Menes et al. |
| 5,025,811 A | 6/1991 | Dobrogowski et al. |
| 5,057,072 A | 10/1991 | Phipps |
| 5,066,276 A | 11/1991 | Wang |
| 5,098,389 A | 3/1992 | Cappucci |
| 5,100,394 A | 3/1992 | Dudar et al. |
| 5,104,381 A | 4/1992 | Gresl et al. |
| 5,137,447 A | 8/1992 | Hunter |
| 5,137,509 A | 8/1992 | Freitas |
| 5,164,188 A | 11/1992 | Wong |
| 5,172,807 A | 12/1992 | Dragan et al. |
| 5,181,909 A | 1/1993 | McFarlane |
| 5,206,267 A | 4/1993 | Shulman |
| 5,211,638 A | 5/1993 | Dudar et al. |
| 5,273,530 A | 12/1993 | Del Cerro et al. |
| 5,279,564 A | 1/1994 | Taylor |
| 5,284,474 A | 2/1994 | Adair |
| 5,292,310 A | 3/1994 | Yoon |
| 5,295,972 A | 3/1994 | Mischenko |
| 5,295,974 A | 3/1994 | O'Laughlin |
| 5,300,084 A | 4/1994 | Johnson |
| 5,312,361 A | 5/1994 | Zadini et al. |
| 5,320,609 A | 6/1994 | Haber et al. |
| 5,354,286 A | 10/1994 | Mesa et al. |
| 5,358,489 A | 10/1994 | Wyrick |
| 5,364,373 A | 11/1994 | Waskonig et al. |
| 5,364,374 A | 11/1994 | Morrison et al. |
| 5,364,734 A | 11/1994 | Pawlowski et al. |
| 5,395,310 A | 3/1995 | Untereker et al. |
| 5,397,313 A | 3/1995 | Gross |
| 5,399,159 A | 3/1995 | Chin et al. |
| 5,401,247 A | 3/1995 | Yoon |
| 5,407,070 A | 4/1995 | Bascos et al. |
| 5,409,457 A | 4/1995 | Del Cerro et al. |
| 5,443,505 A | 8/1995 | Wong et al. |
| 5,454,409 A | 10/1995 | McAffer et al. |
| 5,527,306 A | 6/1996 | Haining |
| 5,538,503 A | 7/1996 | Henley |
| 5,547,467 A | 8/1996 | Pliquett et al. |
| 5,575,780 A | 11/1996 | Saito |
| 5,632,740 A | 5/1997 | Koch et al. |
| 5,658,256 A | 8/1997 | Shields |
| D383,049 S | 9/1997 | Concari et al. |
| 5,667,491 A | 9/1997 | Pliquett et al. |
| 5,681,825 A | 10/1997 | Lindqvist et al. |
| 5,752,942 A | 5/1998 | Doyle et al. |
| 5,766,198 A | 6/1998 | Li |
| 5,766,242 A | 6/1998 | Wong et al. |
| 5,767,079 A | 6/1998 | Glaser et al. |

(56) References Cited

U.S. PATENT DOCUMENTS

| | | |
|---|---|---|
| 5,779,668 A | 7/1998 | Grabenkort |
| 5,788,679 A | 8/1998 | Gravlee, Jr. |
| 5,792,099 A | 8/1998 | DeCamp et al. |
| 5,817,075 A | 10/1998 | Giungo |
| 5,824,072 A | 10/1998 | Wong |
| 5,839,715 A | 11/1998 | Leinsing |
| 5,893,397 A | 4/1999 | Peterson et al. |
| 5,911,223 A | 6/1999 | Weaver et al. |
| 5,919,158 A | 7/1999 | Saperstein et al. |
| 5,951,520 A | 9/1999 | Burzynski et al. |
| 5,952,378 A | 9/1999 | Stjernschantz et al. |
| 5,968,022 A | 10/1999 | Saito |
| 6,003,566 A | 12/1999 | Thibault et al. |
| 6,039,093 A | 3/2000 | Mrotzek et al. |
| 6,059,111 A | 5/2000 | Davila et al. |
| 6,083,199 A | 7/2000 | Thorley et al. |
| 6,139,534 A | 10/2000 | Niedospial, Jr. et al. |
| 6,143,329 A | 11/2000 | Kim |
| 6,149,623 A | 11/2000 | Reynolds |
| 6,154,671 A | 11/2000 | Parel et al. |
| 6,159,218 A | 12/2000 | Aramant et al. |
| 6,189,580 B1 | 2/2001 | Thibault et al. |
| 6,209,738 B1 | 4/2001 | Jansen et al. |
| 6,258,078 B1 | 7/2001 | Thilly |
| 6,280,470 B1 | 8/2001 | Peyman |
| 6,299,603 B1 | 10/2001 | Hecker et al. |
| 6,309,347 B1 | 10/2001 | Takahashi et al. |
| 6,309,374 B1 | 10/2001 | Hecker et al. |
| 6,319,225 B1 | 11/2001 | Sugita et al. |
| 6,319,240 B1 | 11/2001 | Beck |
| 6,334,856 B1 | 1/2002 | Allen et al. |
| 6,378,526 B1 | 4/2002 | Bowman et al. |
| 6,378,714 B1 | 4/2002 | Jansen et al. |
| 6,379,340 B1 | 4/2002 | Zinger et al. |
| 6,387,078 B1 | 5/2002 | Gillespie, III |
| 6,397,849 B1 | 6/2002 | Bowman et al. |
| 6,413,245 B1 | 7/2002 | Yaacobi et al. |
| 6,432,090 B1 | 8/2002 | Brunel |
| 6,491,670 B1 | 12/2002 | Toth et al. |
| 6,494,865 B1 | 12/2002 | Alchas |
| 6,503,231 B1 | 1/2003 | Prausnitz et al. |
| 6,503,240 B1 | 1/2003 | Niedospial, Jr. et al. |
| 6,517,523 B1 | 2/2003 | Kaneko et al. |
| 6,524,581 B1 | 2/2003 | Adamis |
| 6,530,904 B1 | 3/2003 | Edwards et al. |
| 6,540,725 B1 | 4/2003 | Ponzi |
| 6,544,246 B1 | 4/2003 | Niedospial, Jr. |
| 6,546,283 B1 | 4/2003 | Beck et al. |
| 6,551,299 B2 | 4/2003 | Miyoshi et al. |
| 6,558,361 B1 | 5/2003 | Yeshurun |
| 6,564,630 B1 | 5/2003 | Klemp |
| 6,568,439 B1 | 5/2003 | Se et al. |
| 6,569,123 B2 | 5/2003 | Alchas et al. |
| 6,571,837 B2 | 6/2003 | Jansen et al. |
| 6,589,202 B1 | 7/2003 | Powell |
| 6,601,721 B2 | 8/2003 | Jansen et al. |
| 6,611,707 B1 | 8/2003 | Prausnitz et al. |
| 6,622,864 B1 | 9/2003 | Debbs et al. |
| 6,626,309 B1 | 9/2003 | Jansen et al. |
| 6,638,244 B1 | 10/2003 | Reynolds |
| 6,656,433 B2 | 12/2003 | Sasso |
| 6,715,520 B2 | 4/2004 | Andreasson et al. |
| 6,729,370 B2 | 5/2004 | Norton et al. |
| 6,738,526 B1 | 5/2004 | Betrisey et al. |
| 6,743,211 B1 | 6/2004 | Prausnitz et al. |
| 6,773,916 B1 | 8/2004 | Thiel et al. |
| D499,153 S | 11/2004 | Kuo |
| 6,832,994 B2 | 12/2004 | Niedospial, Jr. et al. |
| 6,875,205 B2 | 4/2005 | Leinsing |
| 6,883,222 B2 | 4/2005 | Landau |
| 6,918,889 B1 | 7/2005 | Brunel |
| 6,929,623 B2 | 8/2005 | Stone |
| 6,936,053 B1 | 8/2005 | Weiss |
| 6,957,745 B2 | 10/2005 | Thibault et al. |
| 6,979,316 B1 | 12/2005 | Rubin et al. |
| 6,997,917 B2 | 2/2006 | Niedospial, Jr. et al. |
| 7,025,389 B2 | 4/2006 | Cuschieri et al. |
| 7,025,774 B2 | 4/2006 | Freeman et al. |
| 7,150,735 B2 | 12/2006 | Hickle |
| 7,207,965 B2 | 4/2007 | Simon |
| 7,207,980 B2 | 4/2007 | Christian et al. |
| 7,211,062 B2 | 5/2007 | Kwon |
| 7,214,212 B2 | 5/2007 | Pommereau et al. |
| 7,226,439 B2 | 6/2007 | Prausnitz et al. |
| 7,316,676 B2 | 1/2008 | Peyman et al. |
| 7,326,194 B2 | 2/2008 | Zinger et al. |
| 7,425,207 B2 | 9/2008 | Miller et al. |
| 7,435,237 B2 | 10/2008 | Tan |
| 7,468,057 B2 | 12/2008 | Ponzi |
| 7,470,257 B2 | 12/2008 | Norton et al. |
| 7,488,308 B2 | 2/2009 | Lesch, Jr. |
| 7,510,547 B2 | 3/2009 | Fangrow |
| 7,510,548 B2 | 3/2009 | Fangrow |
| D590,690 S | 4/2009 | Bertini |
| D598,543 S | 8/2009 | Vogel et al. |
| 7,569,035 B1 | 8/2009 | Wilmot et al. |
| 7,615,041 B2 | 11/2009 | Sullivan et al. |
| 7,632,261 B2 | 12/2009 | Zinger et al. |
| 7,648,482 B2 | 1/2010 | Edwards et al. |
| 7,648,491 B2 | 1/2010 | Rogers |
| 7,678,077 B2 | 3/2010 | Harris et al. |
| 7,678,078 B1 | 3/2010 | Peyman et al. |
| 7,722,581 B2 | 5/2010 | Peyman |
| 7,799,009 B2 | 9/2010 | Niedospial, Jr. et al. |
| 7,879,018 B2 | 2/2011 | Zinger et al. |
| 7,914,803 B2 | 3/2011 | Chowhan et al. |
| 7,918,814 B2 | 4/2011 | Prausnitz et al. |
| 7,918,874 B2 | 4/2011 | Siegal |
| 7,947,660 B2 | 5/2011 | Clark et al. |
| 7,967,772 B2 | 6/2011 | McKenzie et al. |
| 7,975,733 B2 | 7/2011 | Horppu et al. |
| 7,981,101 B2 | 7/2011 | Walsh |
| 8,003,124 B2 | 8/2011 | Varner et al. |
| 8,009,162 B2 | 8/2011 | Takatori |
| 8,016,809 B2 | 9/2011 | Zinger et al. |
| 8,025,653 B2 | 9/2011 | Capitaine et al. |
| 8,034,105 B2 | 10/2011 | Stegmann et al. |
| 8,070,739 B2 | 12/2011 | Zinger et al. |
| 8,099,162 B2 | 1/2012 | Roy |
| 8,114,110 B2 | 2/2012 | Bednarek et al. |
| 8,123,729 B2 | 2/2012 | Yamamoto et al. |
| 8,123,736 B2 | 2/2012 | Kraushaar et al. |
| 8,128,960 B2 | 3/2012 | Kabra et al. |
| 8,137,312 B2 | 3/2012 | Sundar et al. |
| 8,157,784 B2 | 4/2012 | Rogers |
| 8,162,914 B2 | 4/2012 | Kraushaar et al. |
| 8,167,863 B2 | 5/2012 | Yow |
| 8,172,830 B2 | 5/2012 | Christian et al. |
| 8,173,617 B2 | 5/2012 | Clark et al. |
| 8,177,768 B2 | 5/2012 | Leinsing |
| 8,187,248 B2 | 5/2012 | Zihlmann |
| 8,192,408 B2 | 6/2012 | Nazzaro et al. |
| 8,197,435 B2 | 6/2012 | Prausnitz et al. |
| 8,197,443 B2 | 6/2012 | Sundar et al. |
| 8,197,459 B2 | 6/2012 | Jansen et al. |
| 8,221,353 B2 | 7/2012 | Cormier et al. |
| 8,225,826 B2 | 7/2012 | Horppu et al. |
| 8,235,967 B2 | 8/2012 | Chevallier et al. |
| D667,111 S | 9/2012 | Robinson |
| 8,257,336 B2 | 9/2012 | Zihlmann |
| 8,262,641 B2 | 9/2012 | Vedrine et al. |
| 8,287,494 B2 | 10/2012 | Ma |
| 8,303,599 B2 | 11/2012 | Hess et al. |
| D672,506 S | 12/2012 | Szymanski |
| 8,323,227 B2 | 12/2012 | Hamatake et al. |
| 8,328,772 B2 | 12/2012 | Kinast et al. |
| 8,337,421 B2 | 12/2012 | Freeman et al. |
| 8,337,509 B2 | 12/2012 | Schieber et al. |
| 8,348,924 B2 | 1/2013 | Christian et al. |
| 8,403,941 B2 | 3/2013 | Peterson et al. |
| 8,409,165 B2 | 4/2013 | Niedospial, Jr. et al. |
| 8,425,473 B2 | 4/2013 | Ho et al. |
| 8,430,862 B2 | 4/2013 | Peyman et al. |
| 8,448,786 B2 | 5/2013 | Tomes et al. |

(56) References Cited

U.S. PATENT DOCUMENTS

| | | |
|---|---|---|
| 8,460,242 B2 | 6/2013 | Paques et al. |
| 8,469,939 B2 | 6/2013 | Fangrow, Jr. |
| 8,475,404 B2 | 7/2013 | Foshee et al. |
| 8,480,646 B2 | 7/2013 | Nord et al. |
| 8,506,515 B2 | 8/2013 | Burns et al. |
| 8,512,309 B2 | 8/2013 | Shemesh et al. |
| 8,529,492 B2 | 9/2013 | Clauson et al. |
| 8,535,333 B2 | 9/2013 | De Juan, Jr. et al. |
| 8,540,692 B2 | 9/2013 | Fangrow |
| 8,545,430 B2 | 10/2013 | Silvestrini |
| 8,545,554 B2 | 10/2013 | Novakovic et al. |
| 8,562,545 B2 | 10/2013 | Freeman et al. |
| 8,571,802 B2 | 10/2013 | Robinson et al. |
| 8,574,214 B2 | 11/2013 | Kuhn et al. |
| 8,574,217 B2 | 11/2013 | Peyman |
| 8,602,959 B1 | 12/2013 | Park et al. |
| 8,608,723 B2 | 12/2013 | Lev et al. |
| 8,617,121 B2 | 12/2013 | Lanin et al. |
| 8,628,508 B2 | 1/2014 | Weitzel et al. |
| 8,632,589 B2 | 1/2014 | Helmy |
| 8,636,713 B2 | 1/2014 | Prausnitz et al. |
| 8,652,118 B2 | 2/2014 | Peyman |
| 8,663,167 B2 | 3/2014 | Bartha |
| 8,663,303 B2 | 3/2014 | Horvath et al. |
| 8,668,676 B2 | 3/2014 | Chang |
| 8,685,435 B2 | 4/2014 | Nivaggioli et al. |
| 8,702,659 B2 | 4/2014 | Lanin et al. |
| 8,727,117 B2 | 5/2014 | Maasarani |
| 8,747,365 B2 | 6/2014 | De Sausmarez Lintell |
| 8,752,598 B2 | 6/2014 | Denenburg et al. |
| 8,758,306 B2 | 6/2014 | Lopez et al. |
| 8,795,226 B2 | 8/2014 | Kuhn et al. |
| 8,808,225 B2 | 8/2014 | Prausnitz et al. |
| 8,808,242 B2 | 8/2014 | Paques et al. |
| D713,958 S | 9/2014 | Srinivasan et al. |
| 8,821,870 B2 | 9/2014 | Robinson et al. |
| D715,125 S | 10/2014 | Hung |
| 8,852,137 B2 | 10/2014 | Horvath et al. |
| 8,864,740 B2 | 10/2014 | Schabbach et al. |
| D718,602 S | 12/2014 | Musser |
| D719,256 S | 12/2014 | Ohashi |
| 8,920,375 B2 | 12/2014 | Gonnelli |
| D726,908 S | 4/2015 | Yu et al. |
| D733,289 S | 6/2015 | Blanchard et al. |
| D740,098 S | 10/2015 | Kuo et al. |
| 9,180,044 B2 | 11/2015 | Touchard et al. |
| 9,180,047 B2 | 11/2015 | Andino et al. |
| D750,223 S | 2/2016 | Andino et al. |
| 9,539,139 B2 | 1/2017 | Andino et al. |
| 9,572,800 B2 | 2/2017 | Zarnitsyn et al. |
| 9,636,253 B1 | 5/2017 | Andino et al. |
| 9,636,332 B2 | 5/2017 | Zarnitsyn et al. |
| 9,664,926 B2 | 5/2017 | Mitsui |
| 9,770,361 B2 | 9/2017 | Andino et al. |
| 9,788,995 B2 | 10/2017 | Prausnitz et al. |
| 9,931,330 B2 | 4/2018 | Zarnitsyn et al. |
| 9,937,075 B2 | 4/2018 | Andino et al. |
| 9,956,114 B2 | 5/2018 | Andino et al. |
| 10,188,550 B2 | 1/2019 | Andino et al. |
| 10,390,901 B2 | 8/2019 | Godfrey et al. |
| 10,517,756 B2 | 12/2019 | Andino et al. |
| 10,555,833 B2 | 2/2020 | Andino et al. |
| 10,632,013 B2 | 4/2020 | Prausnitz et al. |
| 10,722,396 B2 | 7/2020 | Andino et al. |
| 10,905,586 B2 | 2/2021 | Prausnitz et al. |
| 10,952,894 B2 | 3/2021 | Hammack et al. |
| 10,973,681 B2 | 4/2021 | Andino et al. |
| 11,559,428 B2 | 1/2023 | Andino et al. |
| 11,596,545 B2 | 3/2023 | Andino et al. |
| 11,752,101 B2 | 9/2023 | Yamamoto et al. |
| 2001/0008961 A1 | 7/2001 | Hecker et al. |
| 2001/0051798 A1 | 12/2001 | Hochman |
| 2002/0042594 A1 | 4/2002 | Lum et al. |
| 2002/0052580 A1 | 5/2002 | Ooyauchi |
| 2002/0082527 A1 | 6/2002 | Liu et al. |
| 2002/0082543 A1 | 6/2002 | Park et al. |
| 2002/0108875 A1 | 8/2002 | Feinberg et al. |
| 2002/0112981 A1 | 8/2002 | Cooper et al. |
| 2002/0142459 A1 | 10/2002 | Williams et al. |
| 2002/0156413 A1 | 10/2002 | Williams et al. |
| 2003/0009113 A1 | 1/2003 | Olson |
| 2003/0050602 A1 | 3/2003 | Pettis et al. |
| 2003/0083645 A1 | 5/2003 | Angel et al. |
| 2003/0088204 A1 | 5/2003 | Joshi |
| 2003/0139729 A1 | 7/2003 | Stegmann et al. |
| 2003/0171722 A1 | 9/2003 | Paques et al. |
| 2003/0233070 A1 | 12/2003 | De La Serna et al. |
| 2004/0019331 A1 | 1/2004 | Yeshurun |
| 2004/0039253 A1 | 2/2004 | Peyman et al. |
| 2004/0049150 A1 | 3/2004 | Dalton et al. |
| 2004/0059256 A1 | 3/2004 | Perez |
| 2004/0072105 A1 | 4/2004 | Yeshurun et al. |
| 2004/0106904 A1 | 6/2004 | Gonnelli et al. |
| 2004/0122359 A1 | 6/2004 | Wenz et al. |
| 2004/0141925 A1 | 7/2004 | Bosch et al. |
| 2004/0164454 A1 | 8/2004 | Gartstein et al. |
| 2004/0186084 A1 | 9/2004 | Alam et al. |
| 2004/0199130 A1* | 10/2004 | Chornenky .......... A61K 31/205 604/289 |
| 2004/0215347 A1 | 10/2004 | Hayes |
| 2004/0249404 A1 | 12/2004 | Haefliger |
| 2004/0265365 A1 | 12/2004 | Daddona et al. |
| 2005/0009910 A1 | 1/2005 | Hughes et al. |
| 2005/0033230 A1 | 2/2005 | Alchas et al. |
| 2005/0055083 A1 | 3/2005 | Carranza et al. |
| 2005/0065137 A1 | 3/2005 | Jani et al. |
| 2005/0070819 A1 | 3/2005 | Poux et al. |
| 2005/0089545 A1 | 4/2005 | Kuwano et al. |
| 2005/0101582 A1 | 5/2005 | Lyons et al. |
| 2005/0101882 A1 | 5/2005 | Leira et al. |
| 2005/0101967 A1 | 5/2005 | Weber et al. |
| 2005/0137525 A1 | 6/2005 | Wang et al. |
| 2005/0148034 A1 | 7/2005 | Hariri et al. |
| 2005/0171507 A1 | 8/2005 | Christian et al. |
| 2005/0181017 A1 | 8/2005 | Hughes et al. |
| 2005/0203575 A1 | 9/2005 | Carson et al. |
| 2005/0209565 A1 | 9/2005 | Yuzhakov et al. |
| 2005/0244462 A1 | 11/2005 | Farooq |
| 2005/0244463 A1 | 11/2005 | Huang et al. |
| 2005/0244469 A1 | 11/2005 | Whitcup et al. |
| 2005/0245906 A1 | 11/2005 | Makower et al. |
| 2005/0256499 A1 | 11/2005 | Pettis et al. |
| 2005/0281862 A1 | 12/2005 | Karakelle et al. |
| 2006/0013859 A1 | 1/2006 | Yamada et al. |
| 2006/0032768 A1 | 2/2006 | Hamai et al. |
| 2006/0036318 A1 | 2/2006 | Foulkes |
| 2006/0055090 A1 | 3/2006 | Lee et al. |
| 2006/0084942 A1 | 4/2006 | Kim et al. |
| 2006/0086689 A1 | 4/2006 | Raju |
| 2006/0089607 A1 | 4/2006 | Chen |
| 2006/0141049 A1 | 6/2006 | Lyons et al. |
| 2006/0173418 A1 | 8/2006 | Rinaudo et al. |
| 2006/0178614 A1 | 8/2006 | Nemati |
| 2006/0189608 A1 | 8/2006 | Bingaman |
| 2006/0195187 A1 | 8/2006 | Stegmann et al. |
| 2006/0202385 A1 | 9/2006 | Xu et al. |
| 2006/0229562 A1 | 10/2006 | Marsh et al. |
| 2006/0233858 A1 | 10/2006 | Tzekov et al. |
| 2006/0259008 A1 | 11/2006 | Orilla |
| 2006/0271025 A1 | 11/2006 | Jones et al. |
| 2007/0016103 A1 | 1/2007 | Calasso et al. |
| 2007/0060927 A1 | 3/2007 | Longson et al. |
| 2007/0073197 A1 | 3/2007 | Prausnitz et al. |
| 2007/0082841 A1 | 4/2007 | Higuchi et al. |
| 2007/0093742 A1 | 4/2007 | Higuchi et al. |
| 2007/0093877 A1 | 4/2007 | Beecham et al. |
| 2007/0129693 A1 | 6/2007 | Hunter et al. |
| 2007/0149944 A1 | 6/2007 | Tashiro et al. |
| 2007/0151882 A1 | 7/2007 | Cocheteux et al. |
| 2007/0178197 A1 | 8/2007 | LaRue et al. |
| 2007/0191863 A1 | 8/2007 | De Juan, Jr. et al. |
| 2007/0202116 A1 | 8/2007 | Burnie et al. |
| 2007/0202186 A1 | 8/2007 | Yamamoto et al. |
| 2007/0224278 A1 | 9/2007 | Lyons et al. |

(56) References Cited

U.S. PATENT DOCUMENTS

| | | |
|---|---|---|
| 2007/0225654 A1 | 9/2007 | Hess et al. |
| 2007/0233037 A1 | 10/2007 | Gifford, III et al. |
| 2007/0260201 A1 | 11/2007 | Prausnitz et al. |
| 2007/0270745 A1 | 11/2007 | Nezhat et al. |
| 2007/0270768 A1 | 11/2007 | Dacquay et al. |
| 2007/0282405 A1 | 12/2007 | Wong, Jr. et al. |
| 2007/0287985 A1 | 12/2007 | Estes et al. |
| 2007/0299386 A1 | 12/2007 | Peyman |
| 2008/0008762 A1 | 1/2008 | Robinson et al. |
| 2008/0015539 A1 | 1/2008 | Pieroni et al. |
| 2008/0027371 A1 | 1/2008 | Higuchi et al. |
| 2008/0033351 A1 | 2/2008 | Trogden et al. |
| 2008/0058704 A1* | 3/2008 | Hee .................. A61F 9/00736 606/4 |
| 2008/0058717 A1 | 3/2008 | Spector |
| 2008/0065002 A1 | 3/2008 | Lobl et al. |
| 2008/0071246 A1 | 3/2008 | Nazzaro et al. |
| 2008/0082841 A1 | 4/2008 | Juenemann et al. |
| 2008/0097335 A1 | 4/2008 | Trogden et al. |
| 2008/0097346 A1 | 4/2008 | Charles |
| 2008/0097390 A1 | 4/2008 | Dacquay et al. |
| 2008/0131484 A1 | 6/2008 | Robinson et al. |
| 2008/0152694 A1 | 6/2008 | Lobl et al. |
| 2008/0177239 A1 | 7/2008 | Li et al. |
| 2008/0183123 A1 | 7/2008 | Behar-Cohen et al. |
| 2008/0200883 A1 | 8/2008 | Tomono |
| 2008/0208255 A1 | 8/2008 | Siegal |
| 2008/0228127 A1 | 9/2008 | Burns et al. |
| 2008/0234625 A1 | 9/2008 | Dacquay et al. |
| 2008/0300634 A1 | 12/2008 | Gray |
| 2009/0030381 A1 | 1/2009 | Lind et al. |
| 2009/0076463 A1 | 3/2009 | Attinger |
| 2009/0081277 A1 | 3/2009 | Robinson et al. |
| 2009/0082321 A1 | 3/2009 | Edelman et al. |
| 2009/0082713 A1 | 3/2009 | Friden |
| 2009/0088721 A1 | 4/2009 | De Bizemont et al. |
| 2009/0105749 A1 | 4/2009 | De Juan et al. |
| 2009/0148527 A1 | 6/2009 | Robinson et al. |
| 2009/0187167 A1 | 7/2009 | Sexton et al. |
| 2009/0259180 A1 | 10/2009 | Choi |
| 2009/0287161 A1 | 11/2009 | Traub et al. |
| 2009/0312782 A1 | 12/2009 | Park |
| 2010/0010004 A1 | 1/2010 | Van Emelen et al. |
| 2010/0010452 A1 | 1/2010 | Paques et al. |
| 2010/0012537 A1 | 1/2010 | Farrar et al. |
| 2010/0015158 A1 | 1/2010 | Robinson et al. |
| 2010/0030150 A1 | 2/2010 | Paques et al. |
| 2010/0057011 A1 | 3/2010 | Charles |
| 2010/0074925 A1 | 3/2010 | Carmon |
| 2010/0074957 A1* | 3/2010 | Robinson .............. A61K 9/1647 424/501 |
| 2010/0081707 A1 | 4/2010 | Ali et al. |
| 2010/0098772 A1 | 4/2010 | Robinson et al. |
| 2010/0100054 A1 | 4/2010 | Cormier et al. |
| 2010/0152646 A1 | 6/2010 | Girijavallabhan et al. |
| 2010/0152667 A1 | 6/2010 | Kietzmann |
| 2010/0152676 A1 | 6/2010 | Clements et al. |
| 2010/0160889 A1 | 6/2010 | Smith et al. |
| 2010/0173866 A1 | 7/2010 | Hee et al. |
| 2010/0191176 A1 | 7/2010 | Ho et al. |
| 2010/0191177 A1 | 7/2010 | Chang et al. |
| 2010/0211079 A1 | 8/2010 | Aramant |
| 2010/0241102 A1 | 9/2010 | Ma |
| 2010/0256597 A1 | 10/2010 | Prausnitz et al. |
| 2010/0312120 A1 | 12/2010 | Meier |
| 2010/0318034 A1 | 12/2010 | Goncalves |
| 2011/0004265 A1 | 1/2011 | Wenger et al. |
| 2011/0022023 A1 | 1/2011 | Weitzel et al. |
| 2011/0060310 A1 | 3/2011 | Prestrelski et al. |
| 2011/0112546 A1 | 5/2011 | Juan, Jr. et al. |
| 2011/0152775 A1 | 6/2011 | Lopez et al. |
| 2011/0166531 A1 | 7/2011 | Stroumpoulis et al. |
| 2011/0202012 A1 | 8/2011 | Bartlett |
| 2011/0213317 A1 | 9/2011 | Chen et al. |
| 2011/0238075 A1 | 9/2011 | Clauson et al. |
| 2011/0243999 A1 | 10/2011 | Dellamary et al. |
| 2011/0264028 A1 | 10/2011 | Ramdas et al. |
| 2011/0282298 A1 | 11/2011 | Agian et al. |
| 2011/0288492 A1 | 11/2011 | Holmqvist |
| 2011/0295152 A1 | 12/2011 | Sasaki et al. |
| 2011/0306923 A1 | 12/2011 | Roy |
| 2012/0004245 A1 | 1/2012 | May et al. |
| 2012/0008327 A1 | 1/2012 | Brennan et al. |
| 2012/0024987 A1 | 2/2012 | Nagele Nacken |
| 2012/0029360 A1 | 2/2012 | Hendriks et al. |
| 2012/0035524 A1 | 2/2012 | Silvestrini |
| 2012/0059346 A1 | 3/2012 | Sheppard et al. |
| 2012/0078224 A1 | 3/2012 | Lerner et al. |
| 2012/0083727 A1 | 4/2012 | Barnett |
| 2012/0095414 A1 | 4/2012 | Lanin et al. |
| 2012/0095438 A1 | 4/2012 | Lanin et al. |
| 2012/0101475 A1 | 4/2012 | Wilmot et al. |
| 2012/0116306 A1 | 5/2012 | Heald et al. |
| 2012/0123351 A1 | 5/2012 | Lanin et al. |
| 2012/0123386 A1 | 5/2012 | Tsals |
| 2012/0123437 A1 | 5/2012 | Horvath et al. |
| 2012/0123440 A1 | 5/2012 | Horvath et al. |
| 2012/0123473 A1 | 5/2012 | Hernandez |
| 2012/0130207 A1 | 5/2012 | O'Dea et al. |
| 2012/0136318 A1 | 5/2012 | Lanin et al. |
| 2012/0150128 A1 | 6/2012 | Zhao |
| 2012/0157880 A1 | 6/2012 | Haselby et al. |
| 2012/0165723 A1 | 6/2012 | Horvath et al. |
| 2012/0191064 A1 | 7/2012 | Conston et al. |
| 2012/0197208 A1 | 8/2012 | Bruggemann et al. |
| 2012/0197218 A1 | 8/2012 | Timm |
| 2012/0203193 A1 | 8/2012 | Rogers |
| 2012/0220917 A1 | 8/2012 | Silvestrini et al. |
| 2012/0226260 A1 | 9/2012 | Prausnitz et al. |
| 2012/0232522 A1 | 9/2012 | Prausnitz et al. |
| 2012/0259288 A1 | 10/2012 | Wagner et al. |
| 2012/0265149 A1 | 10/2012 | Lerner et al. |
| 2012/0271272 A1 | 10/2012 | Hammack et al. |
| 2012/0296307 A1 | 11/2012 | Holt et al. |
| 2013/0035662 A1 | 2/2013 | Decker et al. |
| 2013/0040895 A1 | 2/2013 | Robinson et al. |
| 2013/0041265 A1 | 2/2013 | Sostek et al. |
| 2013/0060202 A1 | 3/2013 | Thorley et al. |
| 2013/0065888 A1 | 3/2013 | Cetina-Cizmek et al. |
| 2013/0072900 A1 | 3/2013 | Colantonio |
| 2013/0079716 A1 | 3/2013 | Thorley et al. |
| 2013/0096533 A1 | 4/2013 | Freeman et al. |
| 2013/0102973 A1 | 4/2013 | Thorley et al. |
| 2013/0116523 A1 | 5/2013 | Jung, II et al. |
| 2013/0138049 A1 | 5/2013 | Kemp et al. |
| 2013/0140208 A1 | 6/2013 | Hemmann |
| 2013/0150803 A1 | 6/2013 | Shetty et al. |
| 2013/0190694 A1 | 7/2013 | Barrow-Williams et al. |
| 2013/0211335 A1 | 8/2013 | Paques et al. |
| 2013/0216623 A1 | 8/2013 | Yamamoto et al. |
| 2013/0218102 A1 | 8/2013 | Iwase et al. |
| 2013/0218269 A1 | 8/2013 | Schachar et al. |
| 2013/0226103 A1 | 8/2013 | Papiorek |
| 2013/0237910 A1 | 9/2013 | Shetty et al. |
| 2013/0237916 A1 | 9/2013 | Hanson et al. |
| 2013/0245600 A1 | 9/2013 | Yamamoto et al. |
| 2013/0253416 A1 | 9/2013 | Rotenstreich |
| 2013/0289545 A1 | 10/2013 | Baerveldt et al. |
| 2013/0295006 A1 | 11/2013 | Christoforidis et al. |
| 2013/0331786 A1 | 12/2013 | Hofmann |
| 2013/0338612 A1 | 12/2013 | Smith et al. |
| 2014/0010823 A1 | 1/2014 | Robinson et al. |
| 2014/0012226 A1 | 1/2014 | Hochman |
| 2014/0018771 A1 | 1/2014 | Shekalim |
| 2014/0027326 A1 | 1/2014 | Peruzzo |
| 2014/0031833 A1 | 1/2014 | Novakovic et al. |
| 2014/0039391 A1 | 2/2014 | Clarke et al. |
| 2014/0039413 A1 | 2/2014 | Jugl et al. |
| 2014/0078854 A1 | 3/2014 | Head et al. |
| 2014/0088552 A1 | 3/2014 | Soni et al. |
| 2014/0094752 A1 | 4/2014 | Hiles |
| 2014/0102927 A1 | 4/2014 | Liversidge |
| 2014/0107566 A1 | 4/2014 | Prausnitz et al. |
| 2014/0114243 A1 | 4/2014 | Smith et al. |

(56) References Cited

U.S. PATENT DOCUMENTS

| | | |
|---|---|---|
| 2014/0124528 A1 | 5/2014 | Fangrow |
| 2014/0135716 A1 | 5/2014 | Clarke et al. |
| 2014/0194834 A1 | 7/2014 | Passaglia |
| 2014/0200518 A1 | 7/2014 | Ekman et al. |
| 2014/0224688 A1 | 8/2014 | Slemmen et al. |
| 2014/0231287 A1 | 8/2014 | Tomes et al. |
| 2014/0236098 A1 | 8/2014 | Mica et al. |
| 2014/0243754 A1 | 8/2014 | Clarke et al. |
| 2014/0249539 A1 | 9/2014 | Mica et al. |
| 2014/0257207 A1 | 9/2014 | Clarke et al. |
| 2014/0261727 A1 | 9/2014 | Mansour et al. |
| 2014/0261877 A1 | 9/2014 | Ivosevic et al. |
| 2014/0276482 A1 | 9/2014 | Astafieva et al. |
| 2014/0276649 A1 | 9/2014 | Ivosevic et al. |
| 2014/0296802 A1 | 10/2014 | Geiger et al. |
| 2014/0309599 A1 | 10/2014 | Schaller |
| 2014/0323979 A1 | 10/2014 | Henley et al. |
| 2014/0323985 A1 | 10/2014 | Hourmand et al. |
| 2014/0330213 A1 | 11/2014 | Hourmand et al. |
| 2014/0350479 A1 | 11/2014 | Hourmand et al. |
| 2014/0353190 A1 | 12/2014 | Okihara et al. |
| 2015/0013827 A1 | 1/2015 | Kuhn |
| 2015/0013835 A1 | 1/2015 | Cordes |
| 2015/0025474 A1 | 1/2015 | Riedel et al. |
| 2015/0038905 A1 | 2/2015 | Andino et al. |
| 2015/0045731 A1 | 2/2015 | Gupta et al. |
| 2015/0045744 A1 | 2/2015 | Gupta et al. |
| 2015/0051545 A1 | 2/2015 | Henderson et al. |
| 2015/0051581 A1 | 2/2015 | Andino et al. |
| 2015/0110717 A1 | 4/2015 | Distel et al. |
| 2015/0129456 A1 | 5/2015 | Miller et al. |
| 2015/0133415 A1 | 5/2015 | Whitcup |
| 2015/0157359 A1 | 6/2015 | Shinzato et al. |
| 2015/0209180 A1 | 7/2015 | Prausnitz et al. |
| 2015/0223977 A1 | 8/2015 | Oberkircher et al. |
| 2015/0258120 A1 | 9/2015 | Zarnitsyn et al. |
| 2015/0297609 A1 | 10/2015 | Shah et al. |
| 2015/0320596 A1 | 11/2015 | Gifford, III et al. |
| 2016/0015895 A1 | 1/2016 | Blondino et al. |
| 2016/0015908 A1 | 1/2016 | Uemura et al. |
| 2016/0022486 A1 | 1/2016 | Clauson et al. |
| 2016/0106584 A1 | 4/2016 | Andino et al. |
| 2016/0106587 A1 | 4/2016 | Jarrett et al. |
| 2016/0166819 A1 | 6/2016 | Simmers |
| 2016/0193080 A1 | 7/2016 | Hammack et al. |
| 2016/0199581 A1 | 7/2016 | Cachemaille et al. |
| 2016/0206628 A1 | 7/2016 | Zarnitsyn et al. |
| 2016/0213662 A1 | 7/2016 | Zarnitsyn et al. |
| 2016/0310417 A1 | 10/2016 | Prausnitz et al. |
| 2016/0331738 A1 | 11/2016 | Jarrett et al. |
| 2016/0354239 A1 | 12/2016 | Roy |
| 2016/0354244 A1 | 12/2016 | Horvath et al. |
| 2017/0086725 A1 | 3/2017 | Woo et al. |
| 2017/0095369 A1 | 4/2017 | Andino et al. |
| 2017/0216228 A1 | 8/2017 | Asgharian et al. |
| 2017/0224435 A1 | 8/2017 | Godfrey et al. |
| 2017/0224534 A1 | 8/2017 | Andino et al. |
| 2017/0273827 A1 | 9/2017 | Prausnitz et al. |
| 2017/0290702 A1 | 10/2017 | Yamamoto et al. |
| 2017/0333416 A1 | 11/2017 | Zarnitsyn et al. |
| 2017/0340560 A1 | 11/2017 | Yamamoto et al. |
| 2018/0028358 A1 | 2/2018 | Andino et al. |
| 2018/0028516 A1 | 2/2018 | Zarnitsyn et al. |
| 2018/0042765 A1 | 2/2018 | Noronha et al. |
| 2018/0042767 A1 | 2/2018 | Andino et al. |
| 2018/0092897 A1 | 4/2018 | Zarnitsyn et al. |
| 2018/0325884 A1 | 11/2018 | Zarnitsyn et al. |
| 2018/0333297 A1 | 11/2018 | Andino et al. |
| 2019/0000669 A1 | 1/2019 | Hammack et al. |
| 2019/0231592 A1 | 8/2019 | Andino et al. |
| 2019/0240208 A1 | 8/2019 | Zarnitsyn et al. |
| 2019/0269702 A1 | 9/2019 | White et al. |
| 2019/0290485 A1 | 9/2019 | Andino et al. |
| 2019/0307606 A1 | 10/2019 | Andino et al. |
| 2019/0350755 A1 | 11/2019 | Andino et al. |
| 2020/0030143 A1 | 1/2020 | Andino et al. |
| 2020/0061357 A1 | 2/2020 | Jung et al. |
| 2020/0237556 A1 | 7/2020 | Prausnitz et al. |
| 2020/0330269 A1 | 10/2020 | Bley et al. |
| 2020/0390692 A1 | 12/2020 | Yamamoto et al. |
| 2021/0022918 A1 | 1/2021 | Prausnitz et al. |
| 2021/0169689 A1 | 6/2021 | Bley et al. |
| 2021/0212940 A1 | 7/2021 | Yamamoto et al. |
| 2021/0220173 A1 | 7/2021 | Andino et al. |
| 2021/0366311 A1 | 11/2021 | Fisher et al. |
| 2021/0393436 A1 | 12/2021 | Prausnitz et al. |
| 2022/0062040 A1 | 3/2022 | Hammack et al. |
| 2022/0062041 A1 | 3/2022 | Hammack et al. |
| 2022/0280386 A1 | 9/2022 | Andino et al. |
| 2022/0347014 A1 | 11/2022 | Yamamoto et al. |
| 2023/0157869 A1 | 5/2023 | Andino et al. |
| 2023/0363941 A1 | 11/2023 | Andino et al. |

FOREIGN PATENT DOCUMENTS

| | | |
|---|---|---|
| CN | 1604799 A | 4/2005 |
| CN | 1608587 A | 4/2005 |
| CN | 1674954 A | 9/2005 |
| CN | 1681547 A | 10/2005 |
| CN | 1706365 A | 12/2005 |
| CN | 1736474 A | 2/2006 |
| CN | 1946445 A | 4/2007 |
| CN | 101031256 A | 9/2007 |
| CN | 101052434 A | 10/2007 |
| CN | 101351239 A | 1/2009 |
| CN | 201192452 Y | 2/2009 |
| CN | 101559249 A | 10/2009 |
| CN | 201356711 Y | 12/2009 |
| CN | 201591741 U | 9/2010 |
| CN | 101854891 A | 10/2010 |
| CN | 101959519 A | 1/2011 |
| CN | 103037802 A | 4/2013 |
| CN | 103209733 A | 7/2013 |
| CN | 103857431 A | 6/2014 |
| CN | 204364577 U | 6/2015 |
| EA | 006961 B1 | 6/2006 |
| EP | 1188456 A1 | 3/2002 |
| EP | 1568359 A1 | 8/2005 |
| EP | 2193821 A1 | 6/2010 |
| EP | 2307055 A2 | 4/2011 |
| JP | 2001525826 A | 12/2001 |
| JP | 2009183441 A | 8/2009 |
| JP | 2009531298 A | 9/2009 |
| JP | 2010234034 A | 10/2010 |
| JP | 2013543418 A | 12/2013 |
| JP | 5828535 B1 | 12/2015 |
| KR | 20040096561 A | 11/2004 |
| RU | 14351 U1 | 7/2000 |
| RU | 2344767 C2 | 1/2009 |
| RU | 2353393 C2 | 4/2009 |
| RU | 2428956 C2 | 9/2011 |
| WO | WO-9208406 A1 | 5/1992 |
| WO | WO-9220389 A1 | 11/1992 |
| WO | WO-9401124 A1 | 1/1994 |
| WO | WO-9412217 A1 | 6/1994 |
| WO | WO-9609838 A1 | 4/1996 |
| WO | WO-9851348 A2 | 11/1998 |
| WO | WO-0007530 A2 | 2/2000 |
| WO | WO-0007565 A2 | 2/2000 |
| WO | WO-0117589 A1 | 3/2001 |
| WO | WO-0141685 A2 | 6/2001 |
| WO | WO-02058769 A1 | 8/2002 |
| WO | WO-03002094 A2 | 1/2003 |
| WO | WO-03024507 A2 | 3/2003 |
| WO | WO-03039633 A2 | 5/2003 |
| WO | WO-2004000389 A2 | 12/2003 |
| WO | WO-2004105864 A1 | 12/2004 |
| WO | WO-2005011741 A2 | 2/2005 |
| WO | WO-2005032510 A1 | 4/2005 |
| WO | WO-2005046641 A2 | 5/2005 |
| WO | WO-2005069831 A2 | 8/2005 |
| WO | WO-2005072701 A1 | 8/2005 |
| WO | WO-2005074942 A1 | 8/2005 |
| WO | WO-2005107845 A1 | 11/2005 |

(56) References Cited

FOREIGN PATENT DOCUMENTS

| WO | WO-2006004595 A2 | 1/2006 |
|---|---|---|
| WO | WO-2006020714 A2 | 2/2006 |
| WO | WO-2006042252 A2 | 4/2006 |
| WO | WO-2006058189 A2 | 6/2006 |
| WO | WO-2006128034 A1 | 11/2006 |
| WO | WO-2006138719 A2 | 12/2006 |
| WO | WO-2007069697 A1 | 6/2007 |
| WO | WO-2007099406 A2 | 9/2007 |
| WO | WO-2007100745 A2 | 9/2007 |
| WO | WO-2007130105 A1 | 11/2007 |
| WO | WO-2007131050 A2 | 11/2007 |
| WO | WO-2007150018 A2 | 12/2007 |
| WO | WO-2008082637 A1 | 7/2008 |
| WO | WO-2009067325 A1 | 5/2009 |
| WO | WO-2009105534 A2 | 8/2009 |
| WO | WO-2009114521 A1 | 9/2009 |
| WO | WO-2010009034 A2 | 1/2010 |
| WO | WO-2010054660 A1 | 5/2010 |
| WO | WO-2010132751 A1 | 11/2010 |
| WO | WO-2011057065 A1 | 5/2011 |
| WO | WO-2011123722 A1 | 10/2011 |
| WO | WO-2011139713 A2 | 11/2011 |
| WO | WO-2012019136 A2 | 2/2012 |
| WO | WO-2012051575 A2 | 4/2012 |
| WO | WO-2012118498 A1 | 9/2012 |
| WO | WO-2012125869 A1 | 9/2012 |
| WO | WO-2012125872 A2 | 9/2012 |
| WO | WO-2012162459 A1 | 11/2012 |
| WO | WO-2013050236 A1 | 4/2013 |
| WO | WO-2013098166 A1 | 7/2013 |
| WO | WO-2013151904 A1 | 10/2013 |
| WO | WO-2014028285 A1 | 2/2014 |
| WO | WO-2014036009 A1 | 3/2014 |
| WO | WO-2014179698 A2 | 11/2014 |
| WO | WO-2014197317 A1 | 12/2014 |
| WO | WO-2015015467 A1 | 2/2015 |
| WO | WO-2015095772 A2 | 6/2015 |
| WO | WO-2015110660 A1 | 7/2015 |
| WO | WO-2015195842 A1 | 12/2015 |
| WO | WO-2015196085 A2 | 12/2015 |
| WO | WO-2016042162 A1 | 3/2016 |
| WO | WO-2016042163 A2 | 3/2016 |
| WO | WO-2017120600 A1 | 7/2017 |
| WO | WO-2017120601 A1 | 7/2017 |
| WO | WO-2017139375 A1 | 8/2017 |
| WO | WO-2017190142 A1 | 11/2017 |
| WO | WO-2017192565 A1 | 11/2017 |
| WO | WO-2022076938 A1 | 4/2022 |

OTHER PUBLICATIONS

Al-Shaikh, B. et al., 2007, "Essentials of Anaesthetic Equipment," Edinburgh: Churchill Livingstone, 3rd Edition, 7 pages.
Amaratunga, A. et al., "Inhibition of Kinesin Synthesis and Rapid Anterograde Axonal Transport in Vivo by an Antisense Oligonucleotide," The Journal of Biological Chemistry, Aug. 1993, vol. 268, No. 23, pp. 17427-17430.
Anthem, USA, "Medical Policy. Suprachoroidal Injection of a Pharmacologic Agent," Last Review Date: Nov. 14, 2013, [online]. Retrieved from the Internet: URL: http://www.anthem.com/medicalpolicies/policies/mp_pw_b076412.htm. Retrieved from the Internet on: Oct. 24, 2014, American Medical Association, 3 pages.
Beer, P. J. et al., "Photographic Evidence of Vitreous Wicks After Intravitreal Injections," Retina Today, 2(2):24-39 (Mar. 2007).
Berglin, L. C. et al., "Tracing of Suprachoroidally Microneedle Injected Labled Drugs and Microbeads in Human, Pig and Rabbit Tissue Using Liquid Nitrogen Snap-Freeze Thaw and Lypholization Techniques," Invest Ophthalmol Vis Sci., 51:E-Abstract 5330 (2010), 2 pages.
Brown, D. M., "Aflibercept for Treatment of Diabetic Macular Edema," Retina Today, Jul./Aug. 2011, pp. 59-60.
Bunnelle, E., "Syringe Diameters," [online] 2005. Cchem.berkeley.edu. Available at: http://www.cchem.berkeley.edu/rsgrp/Syringediameters.pdf [Accessed Mar. 11, 2022], 3 pages.
Careforde Healthcare, B Braun Glass Loss-Of-Resistance Syringes # 332158-10cc Glass Loss-Of-Resistance Syringe, Luer Slip Metal Tip, 10/cs, (2014), 2 pages.
Careforde Inc., Careforde Healthcare, Chicago, IL, "B Braun Glass Loss-Of-Resistance Syringes # 332155-5cc Glass Loss-Of-Resistance Syringe, Luer Lock Metal Tip, 10/cs," [online]. Retrieved from the Internet: http://careforde.com/b-braun-glass-loss-of-resistance-syringes-332155-5cc-glass-loss-of-resistance-syringe-luer-lock-metal-tip-10-cs/. Retrieved from the Internet on: Oct. 16, 2014, (2014), 2 pages.
Careforde Inc., Careforde Healthcare, Chicago, IL, "B Braun Perifix Plastic Loss-Of-Resistance Syringes # 332152-8cc Plastic Luer Lock Loss-of-Resistance Syringe, 50/cs," [online]. Retrieved from the Internet: http://careforde.com/b-braun-perifix-plastic-loss-of-resistance-syringes-332152-8cc-plastic-luer-lock-loss-of-resistance-syringe-50-cs/. Retrieved from the Internet on: Oct. 16, 2014, (2014), 2 pages.
Choy, Y. B. et al., "Mucoadhesive microdiscs engineered for ophthalmic drug delivery: effect of particle geometry and formulation on preocular residence time," Investigative Ophthalmology & Visual Science, 49:4808-4815 (2008).
Dinning, W. J., "Steroids and the eye-indications and complications," Postgraduate Medical Journal, vol. 52, 1976, pp. 634-638.
Dogliotti, A. M., "Research and Clinical Observations on Spinal Anesthesia: With Special Reference to the Peridural Technique," Current Researches in Anesthesia & Analgesia, Mar.-Apr. 1933, vol. 12, Issue 2, pp. 59-65.
Doncaster and Bassetlaw Hospitals, NHS Foundation Trust, Department of Ophthalmology, "Intravitreal injection of triamcinolone," Jul. 2010, [online]. Retrieved from the Internet: URL: http://www.dbh.nhs.uk/Library/Patient_Information_Leaflets/WPR32110%20IIT%20No%20crops.pdf, 2 pages.
Edwards, A. et al., "Fiber matrix model of sclera and corneal stroma for drug delivery to the eye," AIChE Journal, 44(1):214-225 (1998).
Einmahl, et al., "Evaluation of a novel biomaterial in the suprachoroidal space of the rabbit eye" Investigative Ophthalmology & Visual Science, vol. 43, Issue 5, 2002, pp. 1533-1539.
Einmahl, S. et al., "Ocular biocompatibility of a poly(ortho ester) characterized by autocatalyzed degradation," J. Biomed. Mater. Res., 67(1):44-53 (2003).
"Epidural," Wikipedia [online], retrieved from the internet on Sep. 3, 2014, URL: http:/en.wikipedia.org/wiki/Epidural, 21 pages.
Examination Report for Indian Application No. 201917009102, dated Jul. 16, 2021, 6 pages.
Examination Report for Singapore Application No. 11201509051V, dated Feb. 1, 2017, 4 pages.
Examination Report No. 1 for Australian Application No. 2014259694, dated May 24, 2018, 2 pages.
Examination Report No. 1 for Australian Application No. 2015230874, dated Jul. 28, 2017, 11 pages.
Extended European Search Report for European Application No. 07751620.1, dated Jan. 15, 2013, 10 pages.
Extended European Search Report for European Application No. 11777924.9, dated Feb. 4, 2015, 7 pages.
Extended European Search Report for European Application No. 13833318.2, dated Apr. 1, 2016, 7 pages.
Extended European Search Report for European Application No. 14791646.4, dated Nov. 21, 2016, 6 pages.
Extended European Search Report for European Application No. 14808034.4, dated Jan. 23, 2017, 7 pages.
Extended European Search Report for European Application No. 15810459.6, dated Apr. 16, 2018, 11 pages.
Extended European Search Report for European Application No. 17750694.6, dated Sep. 2, 2019, 6 pages.
Extended European Search Report for European Application No. 17880800.2, dated Jun. 2, 2020, 13 pages.
Extended European Search Report for European Application No. 18176149.5, dated Jan. 22, 2019, 10 pages.
Extended European Search Report for European Application No. 18176172.7, dated Feb. 6, 2019, 11 pages.

(56) References Cited

OTHER PUBLICATIONS

Extended European Search Report for European Application No. 18199418.7, dated Jul. 5, 2019, 9 pages.
Falkenstein, I. A. et al., "Comparison of visual acuity in macular degeneration patients measured with Snellen and Early Treatment Diabetic Retinopathy study charts," Ophthalmology 115(2):319-323 (Feb. 2008).
Feldkamp, L. A. et al., "Practical cone-beam algorithm," J. Opt. Soc. Am. A, 1(6):612-619 (1984).
Final Office Action for U.S. Appl. No. 17/711,495 dated Jan. 17, 2023, 36 pages.
Final Rejection Office Action for U.S. Appl. No. 16/178,162 dated May 16, 2022, 55 pages.
Final Rejection Office Action for U.S. Appl. No. 17/523,168 dated Aug. 30, 2022, 20 pages.
First Examination Report for Indian Application No. 10270/DELNP/2015, dated Apr. 5, 2021, 7 pages.
First Examination Report for Indian Application No. 3345/KOLNP/2008, dated May 21, 2015, 3 pages.
First Office Action for Chinese Application No. 200780014501.3, dated Mar. 11, 2010, 6 pages.
First Office Action for Chinese Application No. 201110093644.6, dated Mar. 26, 2012, 11 pages.
First Office Action for Chinese Application No. 201180060268.9, dated Oct. 10, 2014, 9 pages.
First Office Action for Chinese Application No. 201480025034.4, dated Apr. 24, 2018, 10 pages.
First Office Action for Chinese Application No. 201510144330.2, dated Apr. 5, 2016, 17 pages.
First Office Action for Chinese Application No. 201610805842.3, dated Jul. 21, 2017, 4 pages.
First Office Action for Chinese Application No. 201780062253.3, dated Dec. 25, 2020, 22 pages.
First Office Action for Chinese Application No. 201910430078.X, dated Feb. 1, 2021, 8 pages.
Furrer, P. et al., "Ocular tolerance of preservatives and alternatives," European Journal of Pharmaceutics and Biopharmaceutics, 53(3):263-280 (2002).
Geroski, D. H. et al., "Drug delivery for posterior segment eye disease," Invest. Ophthalmol. Vis. Sci., 41(5):961-964 (2000).
Gilger, B. C. et al., "Treatment of acute posterior uveitis in a porcine model by injection of triamcinolone acetonide into the suprachoroidal space using microneedles," Investigative Ophthalmology & Visual Science, 54(4):2483-2492 (2013).
Gilger, et al., "A Novel Bioerodible Deep Scleral Lamellar Cyclosporine Implant for Uveitis," Invest Ophthalmol Vis Sci, vol. 47, Issue 6, 2006, pp. 2596-2605.
Habib, A. S. et al., "The AutoDetect Syringe Versus the Glass Syringe for the Loss of Resistance Technique in Parturients," Duke University Medical Center, Durham, North Carolina, Oct. 2007, 2 pages.
Haller, J. A. et al., "Evaluation of the safety and performance of an applicator for a novel intravitreal dexamethasone drug delivery system for the treatment of macular edema," Retina, 29(1):46-51 (2009).
Haller, J. A., "Intraocular Steroids in the Office. New formulations offer preservative-free triamcinolone without relying on compounding pharmacies," Retinal Physician [online]. Retrieved from the Internet: URL: https://www.retinalphysician.com/supplements/2009/february-2009/special-edition/intraocular-steroids-in-the-office, Feb. 1, 2009, 4 pages.
Hanekamp, S. et al., "Inhibition of Corneal and Retinal Angiogenesis by Organic Integrin Antagonists After Intrascleral or Intravitreal Drug Delivery," Invest Ophthalmol Vis. Sci., 43: E-Abstract 3710, ARVO (2002), 2 pages.
Harvardapparatus.com. 2011. Syringe Selection Guide. [online] Available at: https://www.harvardapparatus.com/media/harvard/pdf/Syringe%20Selection%20Guide.pdf , [Accessed Mar. 11, 2022], 4 pages.

Heller, J., Ocular delivery using poly(ortho esters), Adv. Drug. Deliv. Rev., 57(14):2053-2062 (2005).
Hogan et al., Chapter Eight, Choroid, in Histology of the Human Eye, 9 pages (1971).
HomeCEU, "How Does Iontophoresis Work?", [Online], Retrieved from the Internet: https://www.homeceuconnection.com/blog/how-does-iontophoresis-work/, 2018, 5 pages.
International Preliminary Report on Patentability for International Application No. PCT/US2021/054395 dated Apr. 20, 2023, 11 pages.
International Search Report and Written Opinion for International Application No. PCT/US2007/004874, dated Jun. 4, 2008, 6 pages.
International Search Report and Written Opinion for International Application No. PCT/US2007/068055, dated Nov. 7, 2007, 13 pages.
International Search Report and Written Opinion for International Application No. PCT/US2011/033987, dated Feb. 14, 2012, 7 pages.
International Search Report and Written Opinion for International Application No. PCT/US2011/056433, dated Apr. 25, 2012, 17 pages.
International Search Report and Written Opinion for International Application No. PCT/US2013/056863, dated Nov. 26, 2013, 8 pages.
International Search Report and Written Opinion for International Application No. PCT/US2014/036590, dated Dec. 10, 2014, 10 pages.
International Search Report and Written Opinion for International Application No. PCT/US2014/040254, dated Oct. 31, 2014, 9 pages.
International Search Report and Written Opinion for International Application No. PCT/US2015/036715, dated Jan. 19, 2016, 9 pages.
International Search Report and Written Opinion for International Application No. PCT/US2017/017014, dated Apr. 27, 2017, 13 pages.
International Search Report and Written Opinion for International Application No. PCT/US2017/030439, dated Aug. 1, 2017, 12 pages.
International Search Report and Written Opinion for International Application No. PCT/US2017/030609, dated Oct. 6, 2017, 12 pages.
International Search Report and Written Opinion for International Application No. PCT/US2017/046553, dated Dec. 13, 2017, 14 pages.
International Search Report and Written Opinion for International Application No. PCT/US2017/065796, dated Apr. 12, 2018, 9 pages.
International Search Report and Written Opinion for International Application No. PCT/US2021/054395, dated Mar. 14, 2022, 16 pages.
Invitation pursuant to Article 94(3) and Rule 71(1) for European Application No. 07751620.1, dated Feb. 29, 2016, 3 pages.
Invitation to Pay Additional Fees for International Application No. PCT/US2021/054395, dated Dec. 8, 2021, 4 pages.
Invitation to Respond to Written Opinion for Singapore Application No. 200805936-2, dated Oct. 15, 2012, 7 pages.
Jain, A., "Pseudo loss of resistance in epidural space localization: A complication of subcutaneous emphysema or simply a faulty technique," Saudi J. Anaseth, 5(1):108-109 (2011) (Abstract).
Jiang, J. et al., "Coated Microneedles for Drug Delivery to the Eye," Investigative Ophthalmology & Visual Science, 48(9):4038-4043 (2007).
Jiang, J. et al., "Intrascleral drug delivery to the eye using hollow microneedles," Pharmaceutical Research, 26(2):395-403 (2009).
Jiang, J. et al., "Measurement and Prediction of Lateral Diffusion within Human Sclera," Investigative Ophthalmology & Visual Science, 47(7):3011-3016 (2006).
Kadam, R. S. et al., "Suprachoroidal delivery in a rabbit ex vivo eye model: influence of drug properties, regional differences in delivery, and comparison with intravitreal and intracameral routes," Molecular Vision, 19:1198-1210 (May 2013).

(56) References Cited

OTHER PUBLICATIONS

Karim, R. et al., "Interventions for the treatment of uveitic macular edema: a systematic review and meta-analysis," Clinical Ophthalmology, 7:1109-1144 (2013).
Kim, S. H. et al., "Assessment of Subconjunctival and Intrascleral Drug Delivery to the Posterior Segment Using Dynamic Contrast-Enhanced Magnetic Resonance Imaging," Invest Ophthalmol Vis Sci, vol. 48, No. 2, Feb. 2007, pp. 808-814.
Lee, C. H. et al., "Thixotropic property in pharmaceutical formulations," Journal of Controlled Release (2009) 136:88-98.
Lee, S-B et al., "Drug delivery through the sclera: effects of thickness, hydration and sustained release systems," Experimental Eye Research, 78:599-607 (2004).
Lindfield, D. et al., "Suprachoroidal Devices in Glaucoma. The Past, Present, and Future of Surgery for Suprachoroidal Drainage," Cataract & Refractive Surgery Today Europe, [online], Oct. 2013, Retrieved from the Internet: URL: http://bmctoday.net/crstodayeurope/2013/10/article.asp?f=suprachoroidal-devices-in-glaucoma. Retrieved from the Internet on: Oct. 24, 2014, Bryn Mawr Communications LLC, Wayne, PA, USA, 3 pages.
Loewen, N., "The suprachoroidal space in glaucoma surgery," Jul. 2012, 4 pages.
Mansoor, S. et al., "Pharmacokinetics and Biodistribution of Triamcinolone Acetonide Following Suprachoroidal Injection into the Rabbit Eye In Vivo Using a Microneedle," Investigative Ophthalmology & Visual Science, ARVO Annual Meeting Abstract, Apr. 2011, vol. 52, 6585, 2 pages.
Maurice, D., "Review: Practical Issues in Intravitreal Drug Delivery," J. Ocul. Pharmacol. Ther., 17(4):393-401 (2001).
McAllister, D. V. et al., "Microfabricated needles for transdermal delivery of macromolecules and nanoparticles: Fabrication methods and transport studies," Proceedings of the Natural Academy of Science, vol. 100, No. 24, 2003, pp. 13755-13760.
Non-Final Office Action for U.S. Appl. No. 17/208,235 dated Aug. 21, 2023, 20 pages.
Non-Final Office Action for U.S. Appl. No. 17/711,495 dated Sep. 7, 2022, 26 pages.
Non-Final Office Action for U.S. Appl. No. 17/711,495, dated Aug. 2, 2022, 15 pages.
Norman, D., Epidural analgesia using loss of resistance with air versus saline: Does it make a difference? Should we reevaluate our practice?, AANA Journal, 71(6):449-453 (Dec. 2003).
Notice of Opposition for European Application No. 14791646.4, dated Mar. 29, 2022, 38 pages.
Notice of Reasons for Rejection for Japanese Application No. 2016-068174, dated Mar. 1, 2017, 8 pages.
Notice of Reasons for Rejection for Japanese Application No. 2016-512068, dated Mar. 26, 2018, 4 pages.
Notice of Reasons for Rejection for Japanese Application No. 2016-574090, dated Mar. 4, 2019, 18 pages.
Notice of Reasons for Rejection for Japanese Application No. 2018-142345, dated Jun. 6, 2019, 6 pages.
Notice of Reasons for Rejection for Japanese Application No. 2018-557826, dated Mar. 29, 2021, 13 pages.
Notification of Reason for Rejection for Japanese Application No. 2008-556462, dated Jul. 24, 2012, 15 pages.
Notification of Reason(s) for Rejection for Japanese Application No. 2013-534049, dated Sep. 1, 2015, 11 pages.
Office Action for Brazilian Application No. 112012027416-3, dated Nov. 14, 2021, 4 pages.
Office Action for Brazilian Application No. 112015027762-4, dated Jan. 28, 2022, 19 pages.
Office Action for Brazilian Application No. PI 0708133-2, dated Feb. 26, 2019, 11 pages.
Office Action for Canadian Application No. 162010, dated Aug. 25, 2015, 1 page.
Office Action for Canadian Application No. 2797258, dated Nov. 21, 2016, 3 pages.
Office Action for Canadian Application No. 2,882,184, dated Aug. 18, 2020, 3 pages.
Office Action for Canadian Application No. 2,882,184, dated Jan. 24, 2020, 6 pages.
Office Action for Canadian Application No. 2,882,184, dated May 1, 2019, 3 pages.
Office Action for Canadian Application No. 2,911,290, dated Jun. 18, 2020, 5 pages.
Office Action for Canadian Application No. CA20173062845 dated Jul. 21, 2023, 4 pages.
Office Action for Chinese application No. CN201910430078, dated Jul. 7, 2022, 7 pages.
Office Action for Eurasian Application No. 201592109, dated Apr. 1, 2016, 4 pages.
Office Action for Eurasian Application No. 201592109, dated Jan. 31, 2018, 2 pages.
Office Action for European Application No. 07751620.1, dated Dec. 11, 2014, 5 pages.
Office Action for European Application No. 07751620.1, dated Sep. 13, 2013, 7 pages.
Office Action for European Application No. 11776049.6, dated Oct. 25, 2016, 4 pages.
Office Action for European Application No. 11777924.9, dated Oct. 1, 2019, 5 pages.
Office Action for European Application No. 13833318.2, dated Apr. 20, 2021, 4 pages.
Office Action for European Application No. 13833318.2, dated Aug. 26, 2020, 5 pages.
Office Action for European Application No. 14791646.4, dated Dec. 4, 2017, 5 pages.
Office Action for European Application No. 14791646.4, dated Feb. 11, 2020, 5 pages.
Office Action for European Application No. 14791646.4, dated Sep. 17, 2018, 5 pages.
Office Action for European Application No. 14808034.4, dated Nov. 8, 2017, 4 pages.
Office Action for European Application No. 17755007.6, dated Jun. 25, 2021, 6 pages.
Office Action for European Application No. 17880800.2, dated Apr. 14, 2022, 10 pages.
Office Action for European Application No. 18176172.7, dated Feb. 7, 2020, 4 pages.
Office Action for European Application No. 18199418.7, dated May 18, 2022, 5 pages.
Office Action for European Application No. 18199418.7, dated Nov. 10, 2020, 5 pages.
Office Action for Indian Application No. 10099/DELNP/2012, dated Jul. 2, 2019, 5 pages.
Office Action for Israel application No. 1286808, dated Oct. 20, 2022, 7 pages.
Office Action for Israeli Application No. 242395, dated Aug. 10, 2020, 12 pages.
Office Action for Israeli Application No. 242395, dated May 7, 2019, 7 pages.
Office Action for Israeli Application No. 264764, dated Feb. 28, 2022, 7 pages.
Office Action for Korean Application No. 10-2015-7034411, dated Nov. 16, 2020, 8 pages.
Office Action for Mexican Application No. MX/a/2015/015282, dated May 15, 2019, 8 pages.
Office Action for New Zealand Application No. 714172, dated Dec. 12, 2018, 3 pages.
Office Action for New Zealand Application No. 714172, dated Feb. 1, 2018, 4 pages.
Office Action for New Zealand Application No. 714172, dated Jul. 24, 2018, 4 pages.
Office Action for Russian Application No. 2012147341, dated Feb. 26, 2015, 8 pages.
Office Action for Russian Application No. 2017101660, dated Mar. 5, 2019, 7 pages.
Office Action for U.S. Appl. No. 11/709,941, dated Apr. 12, 2016, 25 pages.
Office Action for U.S. Appl. No. 11/709,941, dated Dec. 14, 2018, 17 pages.

(56) References Cited

OTHER PUBLICATIONS

Office Action for U.S. Appl. No. 11/709,941, dated Dec. 27, 2016, 28 pages.
Office Action for U.S. Appl. No. 11/709,941, dated Feb. 11, 2015, 14 pages.
Office Action for U.S. Appl. No. 11/709,941, dated Jan. 16, 2018, 32 pages.
Office Action for U.S. Appl. No. 11/709,941, dated Jun. 24, 2014, 11 pages.
Office Action for U.S. Appl. No. 11/709,941, dated Mar. 23, 2011, 9 pages.
Office Action for U.S. Appl. No. 11/709,941, dated Oct. 27, 2011, 8 pages.
Office Action for U.S. Appl. No. 11/743,535, dated Aug. 19, 2010, 7 pages.
Office Action for U.S. Appl. No. 11/743,535, dated Dec. 29, 2009, 6 pages.
Office Action for U.S. Appl. No. 12/767,768, dated Jun. 10, 2011, 5 pages.
Office Action for U.S. Appl. No. 13/273,775, dated Feb. 12, 2015, 13 pages.
Office Action for U.S. Appl. No. 13/273,775, dated Jul. 3, 2014, 12 pages.
Office Action for U.S. Appl. No. 13/447,246, dated Oct. 28, 2013, 5 pages.
Office Action for U.S. Appl. No. 13/453,407, dated Mar. 20, 2013, 5 pages.
Office Action for U.S. Appl. No. 13/842,218, dated Jul. 5, 2016, 11 pages.
Office Action for U.S. Appl. No. 13/842,288, dated Oct. 6, 2015, 10 pages.
Office Action for U.S. Appl. No. 14/136,657, dated Dec. 16, 2016, 7 pages.
Office Action for U.S. Appl. No. 14/268,687, dated May 19, 2016, 6 pages.
Office Action for U.S. Appl. No. 14/424,685, dated Dec. 12, 2016, 15 pages.
Office Action for U.S. Appl. No. 14/424,685, dated Jun. 10, 2016, 10 pages.
Office Action for U.S. Appl. No. 14/523,243, dated Feb. 27, 2015, 14 pages.
Office Action for U.S. Appl. No. 14/821,310, dated Jul. 14, 2017, 11 pages.
Office Action for U.S. Appl. No. 14/894,161, dated Apr. 6, 2018, 19 pages.
Office Action for U.S. Appl. No. 14/894,161, dated Dec. 27, 2016, 17 pages.
Office Action for U.S. Appl. No. 14/894,161, dated Sep. 20, 2017, 21 pages.
Office Action for U.S. Appl. No. 15/383,582, dated May 5, 2017, 10 pages.
Office Action for U.S. Appl. No. 15/398,538, dated Apr. 16, 2019, 8 pages.
Office Action for U.S. Appl. No. 15/398,538, dated Jul. 20, 2018, 12 pages.
Office Action for U.S. Appl. No. 15/427,823, dated Apr. 20, 2017, 8 pages.
Office Action for U.S. Appl. No. 15/427,823, dated Jul. 20, 2018, 11 pages.
Office Action for U.S. Appl. No. 15/427,823, dated Sep. 27, 2017, 7 pages.
Office Action for U.S. Appl. No. 15/619,065, dated Jan. 28, 2020, 24 pages.
Office Action for U.S. Appl. No. 15/619,065, dated Jun. 11, 2021, 18 pages.
Office Action for U.S. Appl. No. 15/619,065, dated Jun. 13, 2019, 30 pages.
Office Action for U.S. Appl. No. 15/619,065, dated Nov. 27, 2020, 23 pages.
Office Action for U.S. Appl. No. 15/675,035, dated Jun. 11, 2020, 14 pages.
Office Action for U.S. Appl. No. 15/708,779, dated Jul. 15, 2019, 8 pages.
Office Action for U.S. Appl. No. 15/872,206, dated May 1, 2020, 8 pages.
Office Action for U.S. Appl. No. 15/872,206, dated Oct. 19, 2020, 9 pages.
Office Action for U.S. Appl. No. 15/946,838, dated Jun. 27, 2019, 7 pages.
Office Action for U.S. Appl. No. 16/178,162, dated Jun. 10, 2020, 18 pages.
Office Action for U.S. Appl. No. 16/178,162, dated May 11, 2021, 48 pages.
Office Action for U.S. Appl. No. 16/381,213, dated May 31, 2019, 7 pages.
Office Action for U.S. Appl. No. 16/591,067, dated Nov. 18, 2019, 7 pages.
Office Action for U.S. Appl. No. 16/826,443, dated Jun. 1, 2020, 6 pages.
Office Action for U.S. Appl. No. 17/217,455, dated Jun. 23, 2021, 13 pages.
Office Action for U.S. Appl. No. 17/217,455, dated Oct. 21, 2021, 15 pages.
Office Action for U.S. Appl. No. 17/523,168, dated Mar. 7, 2022, 11 pages.
Olsen, T., "Drug Delivery to the Suprachoroidal Space Shows Promise," Retina Today, pp. 36-39 (Mar./Apr. 2007).
Olsen, T. W. et al., "Cannulation of the Suprachoroidal Space: A Novel Drug Delivery Methodology to the Posterior Segment," American J. Opthamology, 142(5):777-787 (2006).
Ozkiris, A., "Intravitreal Triamcinolone Acetonide Injection for the Treatment of Posterior Uveitis," Ocular Immunology and Inflammation, vol. 14, Issue 4, pp. 233-238 (May 2006), Published online: Jul. 8, 2009 (Abstract).
Partial European Search Report for European Application No. 18176172.7, dated Oct. 30, 2018, 13 pages.
Partial Supplementary European Search Report for European Application No. 15810459.6, dated Dec. 22, 2017, 13 pages.
Patel, S. et al., "Drug Binding to Sclera," Invest Ophthalmol Vis Sci., 50:E-Abstract 5968 (2009), 2 pages.
Patel, S. et al., "Suprachoroidal Drug Delivery Using Microneedles," Invest. Ophthalmol. Vis. Sci., 49:E-Abstract 5006 (2008), 2 pages.
Patel, S. R. et al., "Intraocular Pharmacokinetics of Suprachoroidal Drug Delivery Administered Using Hollow Microneedles," Invest Ophthalmol Vis Sci., 51:E-Abstract 3796 (2010), 2 pages.
Patel, S. R. et al., "Targeted administration into the suprachoroidal space using a microneedle for drug delivery to the posterior segment of the eye," Investigative Ophthalmology & Visual Science, 53(8):4433-4441 (Jul. 2012).
Patel, S. R. et al., "Suprachoroidal drug delivery to the back of the eye using hollow microneedles," Pharmaceutical Research, Sep. 21, 2010, Vo. 28, No. 1, pp. 166-176.
Patel, S. R., "Suprachoroidal drug delivery to the eye using hollow microneedles," Dissertation, Georgia Institute of Technology, May 2011, 177 pages.
Penkov, M. A. et al., "A ten-year experience with usage of the method of supra-choroidal administration of medicinal substances," Oftalmol. Zh., 35(5):281-285 (1980) (Translated from Russian).
Prausnitz, et al., "Permeability of Cornea, Sclera, and Conjunctiva: A Literature Analysis for Drug Delivery to the Eye", Journal of Pharmaceutical Sciences, vol. 87, Issue 12, 1998, pp. 1479-1488.
Prausnitz, M. R. et al., "Measurement and prediction of transient transport across sclera for drug delivery to the eye," Industrial and Engineering Chemistry Research, 37(8):2903-2907 (1998).
Prausnitz, M. R., "Microneedles for Ocular Drug Delivery," Review of Olsen, T., Drug Delivery to the Suprachoroidal Space Shows Promise, Retina Today, Mar./Apr. 2007, p. 39.
Preliminary Office Action for Brazilian Application No. 112012027416-3, dated Jul. 11, 2021, 2 pages.
Preliminary Office Action for Brazilian Application No. 112015027762-4, dated Jan. 17, 2020, 6 pages.

(56) References Cited

OTHER PUBLICATIONS

Preliminary Rejection for Korean Application No. 10-2021-7023167, dated Aug. 17, 2021, 7 pages.
Rowe-Rendleman, C. L. et al., "Prophylactic Intra-Scleral Injection of Steroid Compounds in Rabbit Model of Retinal Neovascularization," Invest Ophthalmol Vis. Sci.,43:E-Abstract 3872, ARVO (2002), 2 pages.
Saberski, L. R. et al., "Identification of the epidural space: Is loss of resistance to air a safe technique? A review of the complications related to the use of air," Regional Anesthesia, 22(1):3-15 (1997).
Sallam, A. et al., "Repeat intravitreal triamcinolone acetonide injections in uveitic macular oedema," Acta Ophthalmologica, 90(4):e323-e325 (2012).
Scott, I. U. et al., "Baseline characteristics and response to treatment of participants with hemiretinal compared with branch retinal or central retinal vein occlusion in the standard care vs. corticosteroid for retinal vein occlusion (SCORE)," Arch. Ophthalmol., 130(12):1517-1524 (Dec. 2012).
Search Report and Written Opinion for Singapore Application No. 11201509051V, dated Nov. 2, 2016, 6 pages.
Search Report and Written Opinion for Singapore Application No. 200805936-2, dated Jun. 8, 2010, 13 pages.
Second Office Action for Chinese Application No. 200780014501.3, dated Aug. 26, 2010, 10 pages.
Second Office Action for Chinese Application No. 201110093644.6, dated Sep. 7, 2012, 8 pages.
Second Office Action for Chinese Application No. 201180060268.9, dated Jun. 18, 2015, 4 pages.
Second Office Action for Chinese Application No. 201510144330.2, dated Dec. 20, 2016, 13 pages.
Second Office Action for Chinese Application No. 201910430078.X, dated Aug. 18, 2021, 5 pages.
Shuler, R. K. et al., "Scleral Permeability of a Small, Single-Stranded Oligonucleotide," Journal of Ocular Pharmacology and Therapeutics, 20(2):159-168 (2004) (Abstract).
Stein, L. et al., "Clinical gene therapy for the treatment of RPE65-associated Leber congenital amaurosis," Expert Opin. Biol. Ther., Mar. 2011, vol. 11, No. 3, pp. 429-439.
Summons to Attend Oral Proceedings Pursuant to Rule 115(1) EPC for European Application No. 07751620.1, mailed Jun. 13, 2017, 8 pages.
Supplementary Search Report for Singapore Application No. 200805936-2, dated May 26, 2011, 8 pages.
Supplementary Search Report for Singapore Application No. 200805936-2, dated May 6, 2011, 8 pages.
Syringepump.com. 2012. NE-300 Just Infusion™ Syringe Pump. [online] Available at: https://www.syringepump.com/download/NE-300Brochure.pdf [Accessed Mar. 11, 2022], 5 pages.
Third Office Action for Chinese Application No. 201110093644.6, dated Dec. 14, 2012, 3 pages.
Third Office Action for Chinese Application No. 201180060268.9, dated Feb. 5, 2016, 6 pages.
Third Office Action for Chinese Application No. 201510144330.2, dated Jun. 28, 2017, 3 pages.
Third Office Action for Chinese Application No. 201910430078.X, dated Mar. 29, 2022, 12 pages.
Wang, P. M. et al., "Minimally Invasive Extraction of Dermal Interstitial Fluid for Glucose Monitoring Using Microneedles," Diabetes Technology & Therapeutics, 7(1):131-141 (2005).
You, X. D. et al., "Chitosan drug delivery system implanting into suprachoroidal space for perforating ocular injury in rabbits," International Journal of Ophthalmology, 5(1):74-76 (2005) [English Abstract].
Final Office Action for U.S. Appl. No. 17/062,096, dated Oct. 25, 2023, 9 pages.
International Search Report and Written Opinion for PCT Application No. PCT/US2023/066324, dated Aug. 7, 2023, 11 pages.
Office Action for Canadian Application No. CA20173072847, dated Sep. 29, 2023, 4 pages.

* cited by examiner

OCULAR INJECTOR AND METHODS FOR ACCESSING SUPRACHOROIDAL SPACE OF THE EYE

CROSS-REFERENCE TO RELATED APPLICATIONS

This application is a continuation of U.S. Utility Application No. 17/711,495, filed Apr. 1, 2022, now U.S. Pat. No. 11,752,101, issued Sep. 12, 2023 which is a continuation of U.S. Utility Application No. 17/217,455, filed Mar. 30, 2021, which is a continuation of U.S. Utility Application No. 16/741,473, filed Jan. 13, 2020, which is a continuation of U.S. Utility Application No. 11/709,941, filed Feb. 21, 2007, which claims priority and the benefit of U.S. Provisional No. 60/776,903, filed Feb. 22, 2006, each of the disclosures of which is incorporated herein by reference in its entirety.

FIELD OF THE INVENTION

The invention relates to the field of drug delivery into the eye.

BACKGROUND OF INVENTION

The eye is a complex organ with a variety of specialized tissues that provide the optical and neurological processes for vision. Accessing the eye for medical treatment is hindered by the small size and delicate nature of the tissues. The posterior region of the eye, including the retina, macula and optic nerve, is especially difficult to access due to the recessed position of the eye within the orbital cavity. In addition, topical eye drops penetrate poorly into the posterior region, further restricting treatment options.

The suprachoroidal space is a potential space in the eye that is located between the choroid, which is the inner vascular tunic, and the sclera, the outer layer of the eye. The suprachoroidal space extends from the anterior portion of the eye near the ciliary body to the posterior end of the eye near the optic nerve. Normally the suprachoroidal space is not evident due to the close apposition of the choroid to the sclera from the intraocular pressure of the eye. Since there is no substantial attachment of the choroid to the sclera, the tissues separate to form the suprachoroidal space when fluid accumulation or other conditions occur. The suprachoroidal space provides a potential route of access from the anterior region of the eye to treat the posterior region.

The present invention is directed to drug formulations for administration to the suprachoroidal space and an apparatus to deliver drugs and other substances in minimally invasive fashion to the suprachoroidal space.

SUMMARY

Drug formulations are provided characterized by a zero shear viscosity of at least 300,000 mPas. A subclass of the drug formulations is further characterized by a viscosity of not more than about 400 mPas at 1000 s$^{-1}$ shear rate.

For injection into the suprachoroidal space of an eye comprising a biologically active substance and a thixotropic polymeric excipient that acts as a gel-like material to spread after injection and uniformly distribute and localize the drug in a region of the suprachoroidal space. In one embodiment, gel-like material crosslinks after injection into the suprachoroidal space. The biologically active substance may comprise microparticles or microspheres. The polymeric excipient may comprise hyaluronic acid, chondroitin sulfate, gelatin, polyhydroxyethylmethacrylate, dermatin sulfate, polyethylene oxide, polyethylene glycol, polypropylene oxide, polypropylene glycol, alginate, starch derivatives, a water soluble chitin derivative, a water soluble cellulose derivative or polyvinylpyrollidone.

In another embodiment, a drug formulation is provided for delivery to the suprachoroidal space of an eye comprising a biologically active substance and microspheres with an outer diameter in the range of about 1 to 33 microns. The microparticles or microspheres additionally may comprise a controlled release coating and/or a tissue affinity surface.

The biologically active substance preferably comprises an antibiotic, 'a steroid, a non-steroidal anti-inflammatory agent, a neuroprotectant, an anti-VEGF agent, or a neovascularization suppressant.

Devices are also provided for minimally invasive delivery of a drug formulation into the suprachoroidal space of the eye comprising a needle having a leading tip shaped to allow passage through scleral tissues without damage to the underlying choroidal tissues, and a sensor to guide placement of the tip to deliver the formulation adjacent to or within the suprachoroidal space.

The sensor may provide an image of the scleral tissues. The sensor preferably responds to ultrasound, light, or differential pressure.

In another embodiment, devices are provided for minimally invasive delivery of a drug formulation into the suprachoroidal space of the eye comprising a needle having a leading tip shaped to allow passage through scleral tissues, and an inner tip that provides an inward distending action to the choroid upon contacting the choroid to prevent trauma thereto.

Methods are provided for administering drugs to the eye comprising placing a formulation comprising a biologically active substance and a polymer excipient in the suprachoroidal space such that the excipient gels after delivery to localize said biologically active substance. The formulation may be placed in a posterior or anterior region of the suprachoroidal space.

In another embodiment, method are provided for administering drugs to a posterior region of the eye comprising placing a formulation comprising a biologically active substance comprising microspheres or microparticles with an outer diameter in the range of about 1 to 33 microns in an anterior region of the suprachoroidal space such that the microspheres or microparticles subsequently migrate to the posterior region. The formulation preferably comprises a polymer excipient to uniformly disperse the microparticles or microspheres in the suprachoroidal space.

In another embodiment, a method is provided of administering drugs in the suprachoroidal space of the eye comprising the steps of placing a needle in scleral tissues toward the suprachoroidal space at a depth of at least half of the scleral thickness, and injecting a drug formulation through the needle into the sclera such that the formulation dissects the scleral tissues adjacent to the suprachoroidal space and enters the suprachoroidal space.

In the methods disclosed herein, the formulation preferably comprises a thixotropic polymer.

DESCRIPTION OF THE PREFERRED EMBODIMENTS

Figure 1:
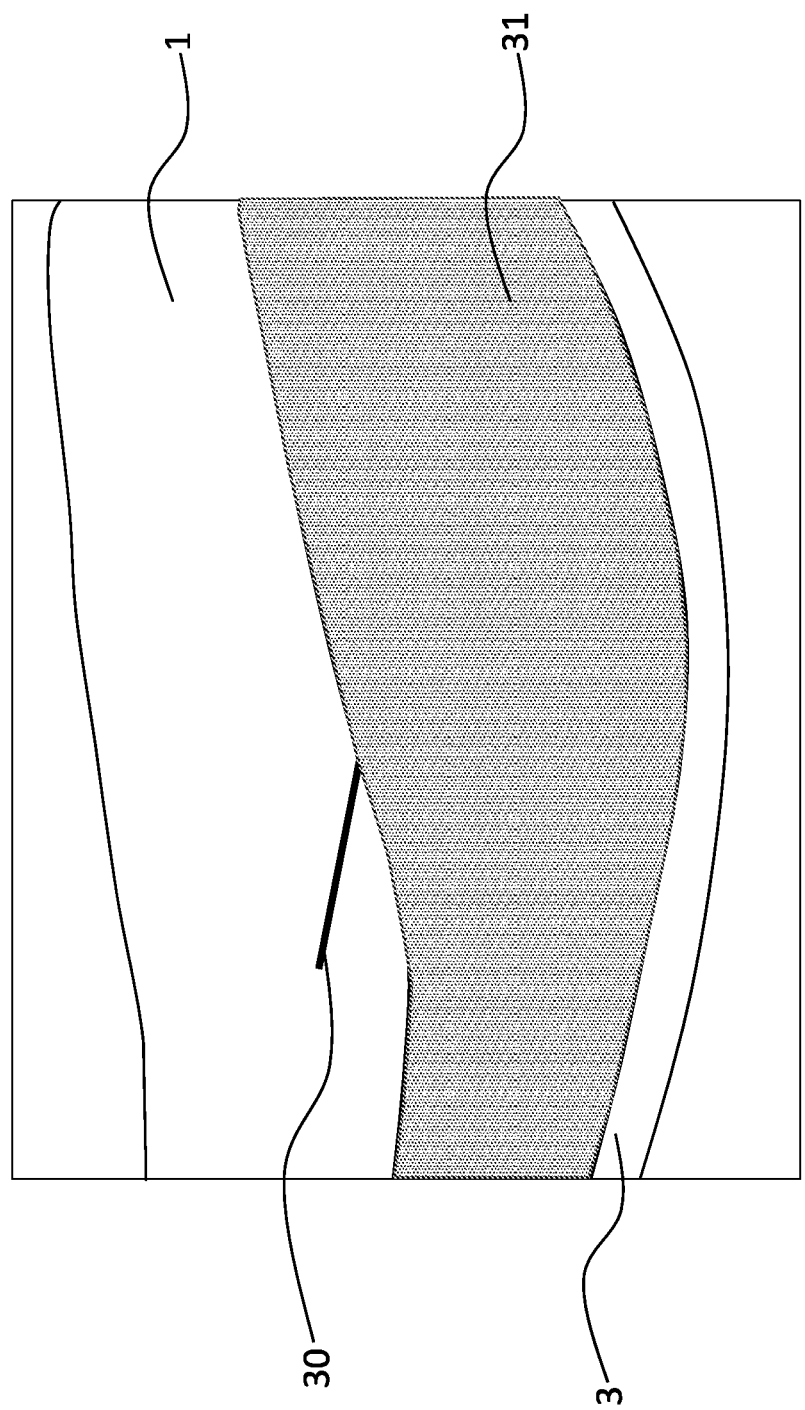
FIG. 1 is an ultrasound image of a portion of the eye after injection by needle into the sclera of a hyaluronic acid surgical viscoelastic material according to Example 9.

The present invention comprises drug formulations, devices and related methods to access the suprachoroidal space of an eye for the purpose of delivering drugs to treat the eye. Specifically, the invention relates to drug formulations designed for suprachoroidal space administration to treat the eye, including specific regions of the eye by localization of the delivered drug. The invention also relates to the design and methods of use for a minimally invasive device to inject drug formulations and drug containing materials directly into the suprachoroidal space through a small needle.

A biologically active substance or material is a drug or other substance that affects living organisms or biological processes, including use in the diagnosis, cure, mitigation, treatment, or prevention of disease or use to affect the structure or any function of the body. A drug formulation contains a biologically active substance.

As used herein, the anterior region of the eye is that region of the eye that is generally readily accessible from the exposed front surface of the eye in its socket. The posterior region of the eye is generally the remaining region of the eye that is primarily surgically accessed through a surface of the eye that is unexposed, thus often requiring temporary retraction of the eye to gain access to that surface.

Formulations:

The drug formulations of the invention provide compatibility with the suprachoroidal space environment and may be formulated to control the distribution of the biologically active substance by migration of the formulation as well as provide for sustained release over time. The drug formulation comprises one or more biologically active substances formulated with physiologically compatible excipients that are administered, typically by injection, into the suprachoroidal space of an eye. Suitable biologically active substances include antibiotics to treat infection, steroids and non-steroidal anti-inflammatory compounds to treat inflammation and edema, neuroprotectant agents such as calcium channel blockers to treat the optic nerve and retinal agents such as anti-VEGF compounds or neo-vascular suppressants to treat macular degeneration.

Formulations for Localized Treatment:

For treatment of a localized region of the eye, for example, to treat a macular lesion, the posterior retina, or the optic nerve, the drug may be prepared in a formulation to limit migration after delivery and delivered to the region of the lesion. While not intending to be bound by a particular theory, we observe that drug microparticles typically travel toward the posterior region of the suprachoroidal space under physiological conditions, presumably due to uveal-scleral fluid flow within the space. Such drug microparticles may be fabricated with sufficient size and optionally with tissue surface affinity to limit drug migration. Tissue surface affinity may be modified by the addition of polymeric or lipid surface coatings to the microparticles, or by the addition of chemical or biological moieties to the microparticle surface. Tissue affinity is thereby obtained from surface charge, hydrophobicity, or biological targeting agents such as antibodies or integrins that may be incorporated to the surface of the microparticles to provide a binding property with the tissues to limit drug migration. Alternatively or in combination, the drug may be formulated with one or more polymeric excipients to limit drug migration. A polymeric excipient may be selected and formulated to act as a viscous gel-like material in-situ and thereby spread into a region of the suprachoroidal space and uniformly distribute and retain the drug. The polymer excipient may be selected and formulated to provide the appropriate viscosity, flow and dissolution properties. For example, carboxymethylcellulose is a weakly thixotropic water soluble polymer that may be formulated to an appropriate viscosity at zero shear rate to form a gel-like material in the suprachoroidal space. The thixotropic effect of the polymer may be enhanced by appropriate chemical modification to the polymer to increase associative properties such as the addition of hydrophobic moieties, the selection of higher molecular weight polymer or by formulation with appropriate surfactants. Preferred is the use of highly associative polymeric excipients with strong thixotropic properties such as hyaluronic acid to maximize the localization and drug retaining properties of the drug formulation while allowing the formulation to be injected through a small gauge needle. The dissolution properties of the drug formulation may be adjusted by tailoring of the water solubility, molecular weight, and concentration of the polymeric excipient in the range of appropriate thixotropic properties to allow both delivery through a small gauge needle and localization in the suprachoroidal space. The polymeric excipient may be formulated to increase in viscosity or to cross-link after delivery to further limit migration or dissolution of the material and incorporated drug. For example, a highly thixotropic drug formulation will have a low viscosity during injection through a small gauge needle, but dramatically increases in effective viscosity once in the supra-choroidal space at zero shear conditions. Hyaluronic acid, a strongly thixotropic natural polymer, when formulated at concentrations of 1 to 2 weight percent demonstrates a viscosity of approximately 300,000 to 7,000,000 mPas at zero shear and viscosity of 150 to 400 mPas at a shear rate of 1000 s$^{-1}$, typical of injection though a small gauge needle, with the exact viscosity depending of the molecular weight. Chemical methods to increase the molecular weight or degree of crosslinking of the polymer excipient may also be used to increase localization of the drug formulation in-situ, for example the formulation of hyaluronic acid with bisepoxide or divinylsulfone crosslinking agents. The environment in the suprachoroidal space may also be used to initiate an increase in viscosity or cross-linking of the polymer excipient, for example from the physiologic temperature, pH or ions associated with the suprachoroidal space. The gel-like material may also be formulated with surface charge, hydrophobicity or specific tissue affinity to limit migration within the suprachoroidal space.

Water soluble polymers that are physiologically compatible are suitable for use as polymeric excipients according to the invention include synthetic polymers such as polyvinylalcohol, polyvinylpyrollidone, polyethylene glycol, polyethylene oxide, polyhydroxyethylmethacrylate, polypropylene glycol and propylene oxide, and biological polymers such as cellulose derivatives, chitin derivatives, alginate, gelatin, starch derivatives, hyaluronic acid, chondroiten sulfate, dermatin sulfate, and other glycosoaminoglycans, and mixtures or copolymers of such polymers. The polymeric excipient is selected to allow dissolution over time, with the rate controlled by the concentration, molecular weight, water solubility, crosslinking, enzyme lability and tissue adhesive properties of the polymer. Especially advantageous are polymer excipients that confer the formulation strong thixotropic properties to enable the drug formulation to exhibit a low viscosity at high shear rates typical of delivery through a small gauge needle to facilitate administration, but exhibit a high viscosity at zero shear to localize the drug in-situ.

To treat an anterior region of the eye, a polymeric excipient to limit drug migration may be combined with a drug and injected into the desired anterior region of the suprachoroidal space.

One method for treating the posterior region of the eye comprises administration of a drug formulation with localizing properties directly to the posterior region of the suprachoroidal space. Drug formulations may be delivered to the posterior region of the suprachoroidal space by using a flexible microcannula placed in an anterior region of the suprachoroidal space with subsequent advancement of the distal tip to the posterior region prior to delivery of the drug and a localizing excipient. Similarly, a flexible microcannula may be advanced to the center of a desired treatment area such as a macular lesion prior to delivery of a drug formulation with properties to localize the administered drug.

Treatment of a localized region of the eye, especially the posterior region, is facilitated by the use of drug preparations of the present invention in combination with administration devices to deliver the preparation locally to various regions of the suprachoroidal space with a flexible device as described in U.S. patent application 60/566,776 by the common inventors, incorporated by reference herein in its entirety.

Formulations for Migration to a Posterior Region:

For treatment of the posterior region of the eye, for example, to treat the entire macula, choroid or the optic nerve, the drug may be prepared in a form to allow migration after delivery and delivered to an anterior region of the suprachoroidal space. The drug may be formulated in soluble form, with a rapid dissoluting polymeric excipient or as small microparticles or microspheres to allow drug migration after administration. If a polymeric excipient is used, a low viscosity, rapidly absorbed formulation may be selected to distribute the drug uniformly in the region of administration to minimize areas of overly high drug concentration, and subsequently dissolution of the excipient to allow drug migration to the posterior region of the suprachoroidal space. Of particular utility is the use of such a polymeric excipient in combination with drug microparticles or microspheres. Such use of drug migration is advantageous as the drug may be injected into an anterior region of the eye easily accessible by the physician, and used to treat a posterior region distant from the injection site such as, the posterior choroid and macula. Preferred microparticles or microspheres are those with an outer diameter in the range of about 1 to 33 microns.

Sustained Release:

The use of drug microparticles, one or more polymeric excipients or a combination of both, may also be applied to confer sustained release properties to the drug formulation. The drug release rate from the microparticles may be tailored by adjusting drug solubility or application of a controlled release coating. The polymeric excipient may also provide sustained release from incorporated drugs. The polymeric excipient may, for example, be selected to limit drug diffusion or provide drug affinity to slow drug release. The dissolution rate of the polymeric excipient may also be adjusted to control the kinetics of its effect on sustained release properties.

Delivery Devices:

A device for minimally invasive delivery of drugs to the suprachoroidal space may comprise a needle for injection of drugs or drug containing materials directly to the suprachoroidal space. The device may also comprise elements to advance the needle through the conjunctiva and sclera tissues to or just adjacent to the suprachoroidal space without perforation or trauma to the inner choroid layer. The position of the leading tip of the delivery device may be confirmed by non-invasive imaging such as ultrasound or optical coherence tomography, external depth markers or stops on the tissue-contacting portion of the device, depth or location sensors incorporated into the device or a combination of such sensors. For example, the delivery device may incorporate a sensor at the leading tip such as a light pipe or ultrasound sensor to determining depth and the location of the choroid or a pressure transducer to determine a change in local fluid pressure from entering the suprachoroidal space.

The leading tip of the delivery device is preferably shaped to facilitate penetration of the sclera, either by cutting, blunt dissection or a combination of cutting and blunt dissection. Features of the device may include energy delivery elements to aid tissue penetration such as ultrasound, high fluid pressure, or tissue ablative energy at the distal tip. The outer diameter of the tissue contacting portion of the device is preferably about the size of a 20 to 25 gauge needle (nominal 0.0358 to 0.0203 inch outer diameter) to allow minimally invasive use without requiring additional features for tissue dissection or wound closure. Suitable materials for the delivery device include high modulus materials such as metals including stainless steel, tungsten and nickel titanium alloys, and structural polymers such as nylon, polyethylene, polypropylene, polyimide and polyetheretherketone, and ceramics. The tissue contacting portions of the device may also comprise surface treatments such as lubricious coatings to assist in tissue penetration or energy reflective or absorptive coatings to aid in location and guidance during medical imaging.

Figure 4:
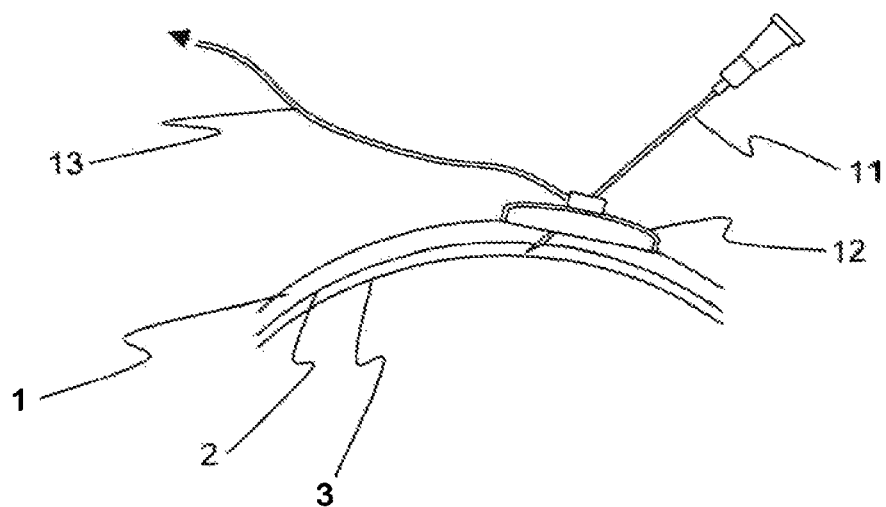
FIG. 4 is a diagram showing the location of a delivery device according to the invention relative to the target sclera, suprachoroidal space and choroid.

The needle may be mounted or slidably disposed at a shallow angle to a plate or fixation mechanism to provide for localization and control of the angle and depth of insertion. The plate, such as shown in FIG. 4, may contain an injection port to allow advancement of the needle through the plate that has been pre-positioned on the surface of the globe (eye surface). The plate may further comprise a vacuum assist seal 12 to provide stabilization of the plate to the target site on the ocular surface. An external vacuum source such as a syringe or vacuum pump is connected by line 13 to the plate to provide suction. The plate should preferably have a bottom side or bottom flanges which are curved suitably to curvature of the globe. The needle 11 is advanced through the sclera 1 until entering the suprachoroidal space 2 but not into choroid 3.

Elements to seal the needle tract during injection such as a flexible flange or vacuum seal along the tract may also be incorporated to aid delivery. Referring to FIG. 4, the location of the delivery device 11 is shown with respect to the target sclera 1, suprachoroidal space 2, and choroid 3 by positioning with a vacuum interfacial seal 12 attached to a suction line 13.

The device may also comprise elements to mechanically open the suprachoroidal space, in order to allow injection of microparticulate drugs or drug delivery implants which are larger than can be delivered with a small bore needle. In one embodiment, such a delivery device may comprise a first element provided to penetrate the scleral tissue to a specified depth, and a second element, which can advance, and atraumatically distend the choroid inwards, maintaining a pathway to the suprachoroidal space. The second element may be disposed within or placed adjacent to the first element. An embodiment of a device having such elements is shown in FIGS. 3a and 3b.

Figure 3A:
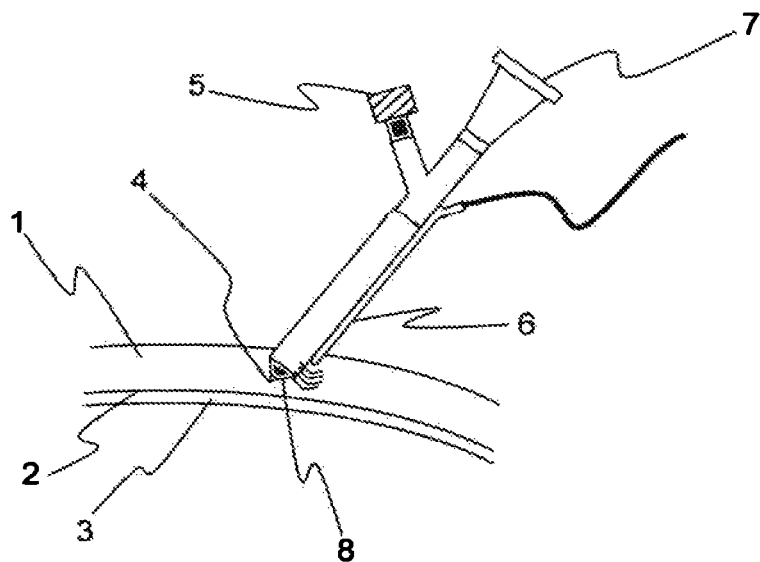
FIGS. 3a and 3b are diagrams of an embodiment of a delivery device according to the invention having a distending and cutting or ablative tip.
Figure 3B:
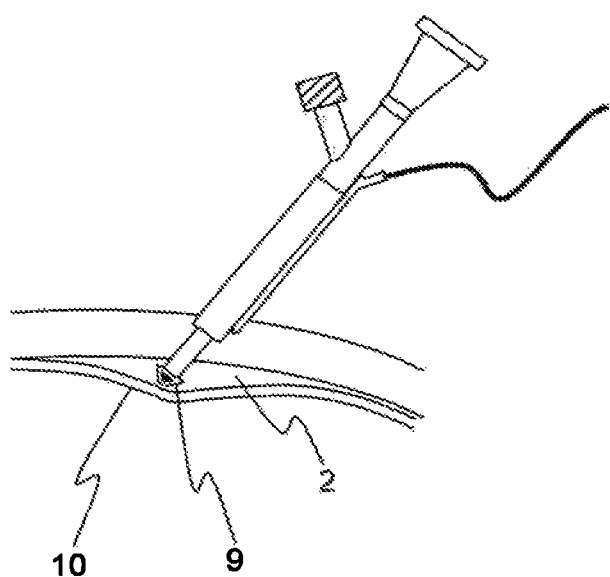

Referring to FIG. 3a a delivery device with a distending tip is shown. The delivery device comprises a cutting or ablative tip 4 a choroidal distention tip 8 at the distal end of the device, and an ultrasonic sensor 6 used to guide the device through the tissues. A luer connector 7 is provided at the proximal end (away from the cutting tip) of the device. The knob 5 is connected to the mechanism for activating the distention tip 8. The device is placed facing the sclera 1 to address the suprachoroidal space 2 adjacent to the choroid 3. The device is then advanced in scleral tissues using the depth sensor for guidance. When the depth sensor indicates that the tip 4 is to or just adjacent to the suprachoroidal space 2, the distension tip 8 is activated to prevent damage to the choroid. Referring to FIG. 3b, the knob 5 has been activated to advance the distention tip to its activated position 9 which results in a distended choroid 10. A pathway to the suprachoroidal space 2 is thereby attained without trauma to the choroid from the ablative tip 4.

In another embodiment, the delivery device comprises a thin walled needle fabricated with a short, high angle bevel at the leading tip to allow the bevel to be advanced into or through scleral tissues. Maintaining the beveled section with the opening directed inward prevents the drug from being expressed away from the suprachoroidal space. Various types of access and delivery may be achieved through the precise placement of the needle tip into or through the scleral tissues. If the needle is advanced through the sclera and into the suprachoroidal space, the needle may then be used for direct injections into the space or to serve as an introducer for the placement of other devices such as a microcannula. If the needle is placed in close proximity to the inner boundary of the sclera, injection of drug formulations through the needle will allow fluid dissection or flow through any remaining interposing scleral tissue and delivery to the suprachoroidal space. An embodiment of a device useful in such manner is shown in FIG. 8.

Figure 5:
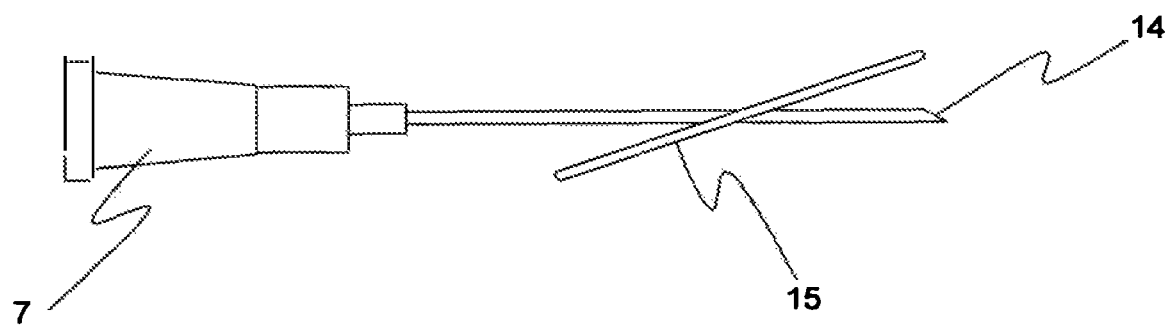
FIG. 5 is a diagram of an embodiment of a delivery device according to the invention having a stop plate to set the depth and angle of penetration of the needle into the eye.
Figure 8:
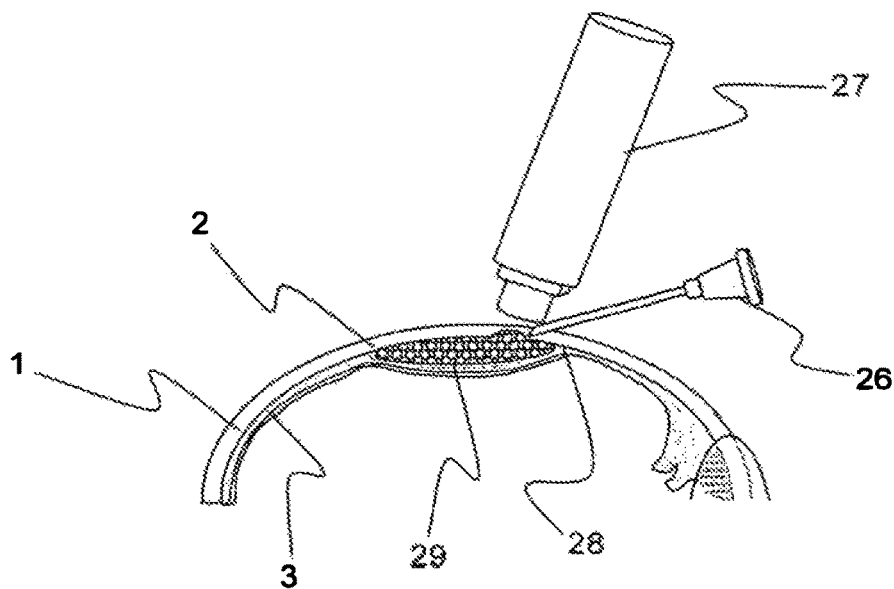
FIG. 8 is a diagram of an embodiment of the use of a device according to the invention in conjunction with a high resolution imaging device to monitor the location of the tip of the cannula.

In FIG. 8, a system to inject a substance into the suprachoroidal space 2 comprises an access cannula 26 and a high resolution imaging device 27. The access cannula may accommodate a hypodermic type needle (not shown) or introducer sheath with a trocar (not shown). Furthermore, the access means may comprise a plate as shown in FIG. 4 or FIG. 5. The access cannula incorporates a beveled sharp distal tip suitably shaped for penetration of the tissues. The imaging device may comprise real-time modalities such as ultrasound, optical coherence tomography (OCT) or microcomputed tomography (MicroCT). The advancement of the access needle or introducer through the sclera is monitored using the imaging device. The access cannula 26 is advanced until the leading tip is in close proximity to the inner boundary of the sclera 28, at which point the injection of the drug is made. Injection of drug formulations through the needle will allow fluid dissection or flow through any remaining interposing scleral tissue and delivery to the suprachoroidal space 29.

In one embodiment, the delivery device may allow a specific angle of entry into the tissues in order to provide a tissue pathway that will maintain the tract within the sclera, or penetrate to the suprachoroidal space without contacting the choroid. Referring to FIG. 5, an embodiment of the device is shown with a luer connector 7 at the proximal end and a bevel needle tip 14 at the distal end. The needle is affixed to an angled stop plate 15 to set the depth and angle of penetration of the needle tip 14. The assembly is advanced until the stop plate encounters the surface of the globe, placing the needle tip at the target depth. The mounting plate may also contain sensors for indicating or directing the position of the needle tip.

Figure 6:
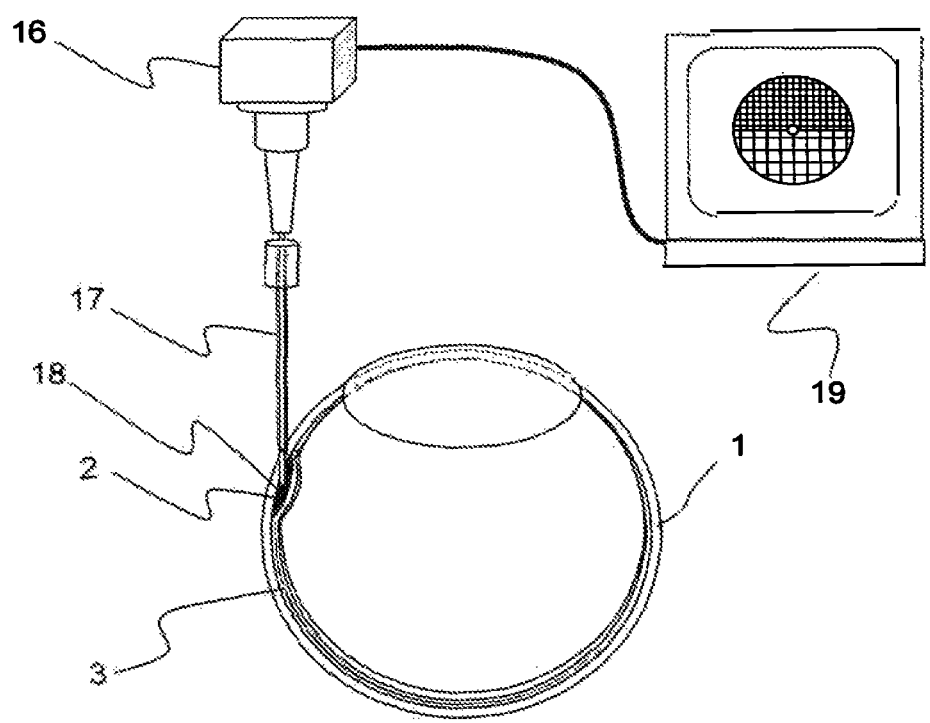
FIG. 6 is a diagram of an embodiment of a delivery device according to the invention that accommodates a microendoscope and camera to monitor the location of the cannula tip during surgery.

In one embodiment, a system for obtaining minimally invasive access to the suprachoroidal space comprises an access cannula and an optical device used to determine the location of the access cannula distal tip in the tissue tract providing direct feedback upon entry to the suprachoroidal space. The color differential between the sclera (white) and the choroid (brown) may be used to provide location information or OCT methods may be used to determine the distance to the choroid interface from the sclera. The optical device may be incorporated within a microcannula, or may be an independent device such as a microendoscope or a fiber optic sensor and transducer capable of detecting the tissue properties. The optical signal may be sent to a camera and monitor for direct visualization, as in the case of an endoscope, or to an optical signal processing system, which will indicate depth by signaling the change in tissue properties at the tip of the optical fiber. The access microcannula may be a needle or introducer-type device made of metal or plastic. The distal end of the access cannula is suitable to pierce ocular tissue. If independent, the optical device will be removed from the access microcannula after cannulation to allow access to the space for other devices or for an injectate to administer treatment. An embodiment of such a system is shown in FIG. 6. The optical device comprises a flexible microendoscope 18, coupled to a CCD camera 16 with the image viewed on a monitor 19. The endoscope is sized to fit slidably in an access cannula 17 that is preferably less than 1 mm in outer diameter. The access cannula 17 comprises a beveled sharp distal tip for tissue access. The distal tip of the endoscope is positioned at the proximal end of the cannula bevel to provide an image of the cannula tip. The cannula is advanced against the ocular surface at the region of the pars plana at a low angle, piercing the sclera 1, and advancing until the endoscope image shows access into the suprachoroidal space 2.

Figure 7:
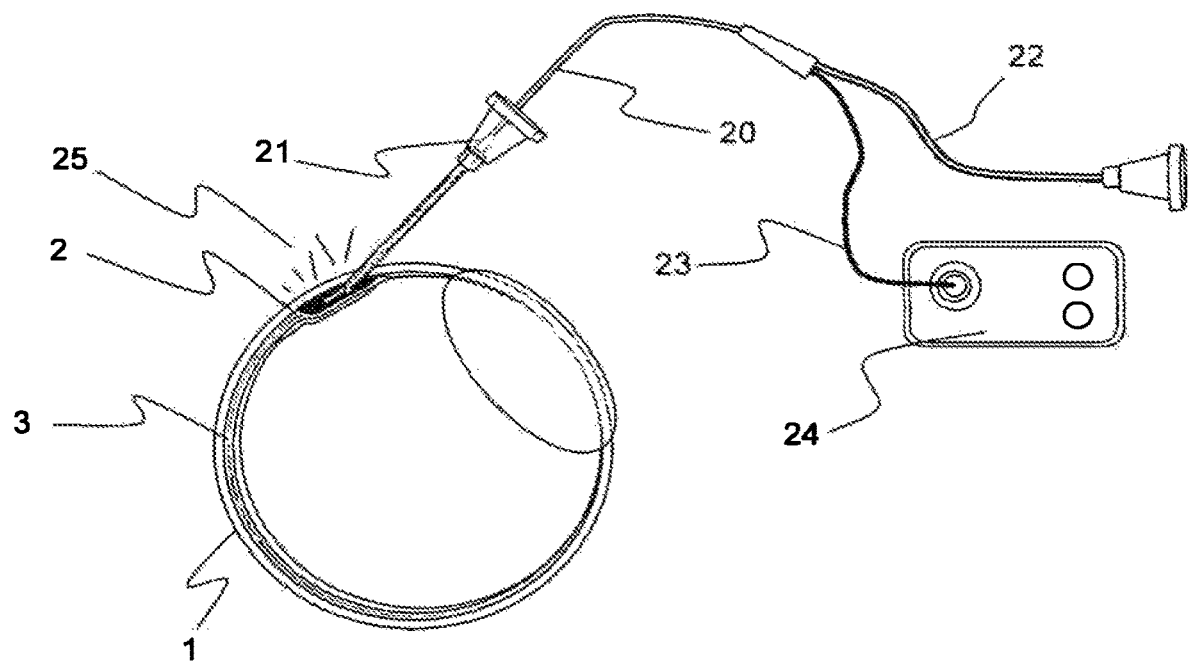
FIG. 7 is a diagram of an embodiment of a delivery device having a lumen for delivery of drugs through a catheter into the eye and a fiber optic line connected to an illumination source to illuminate the tip if the cannula.

In another embodiment, the optical device of the system comprises a focal illumination source at the distal tip. The amount of light scatter and the intensity of the light will vary depending upon the type of tissues and depth of a small light spot traversing the tissues. The change may be seen from the surface by the observing physician or measured with a sensor. The focal spot may be incorporated as an illuminated beacon tip on a microcannula. Referring to FIG. 7, the access device comprises a flexible microcannula or microcatheter 20, sized suitably for atraumatic access into the suprachoroidal space 2. The microcatheter comprises a lumen 22 for the delivery of materials to the space 2 and a fiber optic 23 to provide for an illuminated distal tip. The fiber optic is connected to an illumination source 24 such as a laser diode, superbright LED, incandescent or similar source. The microcatheter is slidably disposed within the access cannula 21. As the access cannula is advanced through the tissues, the light 25 transilluminating the tissues will change. Scleral tissues scatter light from within the sclera tissues to a high degree, however once inside the suprachoroidal space, the light intensity and backscatter seen at the surface diminishes significantly, indicating that the illuminated tip has transited the sclera 1, and is now in the target location at the suprachoroidal space.

Of particular utility with a delivery device are drug formulations as previously described that are compatible with the delivery device. Drug in microparticulate form are preferred to be substantially smaller than the lumen diameter to prevent lumen obstruction during delivery. Microparticles of average outer dimension of approximately 10 to 20% of the device lumen at maximum are preferred. A useful formulation includes microspheres or microparticles with an outer diameter in the range of about 1 to 33 microns. Also preferred is the use of a polymeric excipient in the drug formulation to enable the formulation to be injected into the scleral tissues adjacent to the suprachoroidal space, with subsequent dissection of the tissue between the distal tip and the suprachoroidal space by the excipient containing fluid to form a flow path for the drug into the suprachoroidal space. Formulations with thixotropic properties are advantageous for passage through a small needle lumen as well as for fluid dissection of scleral tissue.

The following examples are provided only for illustrative purposes and are not intended to limit the invention in any way.

Example 1

Fluorescent dyed polystyrene microspheres (Firefli™, Duke Scientific, Inc., Palo Alto, CA) suspended in phosphate-buffered saline were used as model drug to evaluate the size range in which particulates will migrate in the suprachoroidal space from the anterior region to the posterior region.

An enucleated human cadaver eye was radially incised to the choroid in the pars plana region, which is in the anterior portion of the eye. Using a syringe terminated with a blunt 27 gauge needle, 0.15 mL of a 1% by volume microsphere suspension (mean diameter 6 micron) was delivered into the anterior region of the suprachoroidal space. The needle was withdrawn and the incision sealed with cyanoacrylate adhesive.

The eye was then perfused for 24 hours with phosphate buffered saline at 10 mm Hg pressure by introducing into the anterior chamber a 30 gauge needle attached to a reservoir via infusion tubing. The reservoir was placed on a lab jack and elevated to provide constant perfusion pressure. Several hours prior to examination, the eye was placed into a beaker of glycerin to clarify the scleral tissue by dehydration, allowing direct visualization of the suprachoroidal space.

The microspheres were visualized using a stereofluorescence microscope (Model MZ-16, Leica, Inc.) with fluorescence filters selected for the microsphere fluorescence. Under low magnification (7 to 35×) the microspheres could be clearly seen in a stream-like pattern running from the site of instillation back toward the optic nerve region, collecting primarily in the posterior region of the suprachoroidal space.

The experiment was repeated using microsphere suspensions of 1, 6, 10, 15, 24 and 33 micron diameter with the same resulting pattern of migration and distribution to the posterior region of the eye.

Example 2

The experiment of Example 1 was repeated, except that a mixture of 6 and 33 micron diameter fluorescent microspheres as a model drug was suspended in a polymeric excipient comprising a surgical viscoelastic (Healon 5, Advanced Medical Optics, Inc.), a 2.3% concentration of sodium hyaluronic acid of 4,000,000 Daltons molecular weight, with thixotropic properties of a zero shear viscosity of 7,000,000 mPas and 400 mPas viscosity at 1000 s1 shear rate. The mixture was introduced into the suprachoroidal space in the manner of Example 1. After 24 hour perfusion, the microspheres resided solely in the suprachoroidal space at the anterior instillation site and did not show evidence of migration, demonstrating the localizing effect of the thixotropic polymeric excipient.

Example 3

To demonstrate the effect of polymeric excipient viscosity on drug localization, the experiment of Example 1 was repeated, except that bevacizumab (Avastin™, Genentech), an anti-VEG antibody, was adsorbed onto 5 micron diameter carboxylated fluorescent microspheres and mixed at equal volumes with one of three hyaluronic acid based surgical viscoelastics (Healon, Healon GV, Healon 5, Advanced Medical Optics, Inc.), each with a different viscosity and thixotropic properties. (Healon, 300,000 mPas viscoscity at zero shear rate, 150 mPas viscosity at 1000 $s^{-1}$ shear rate; Healon GV, 3,000,000 mPas viscosity at zero shear rate, 200 mPas at $1000s^{-1}$ shear rate; Healon 5, 7,000,000 mPas viscosity at zero shear rate, 400 mPas viscosity at 1000 $s^{-1}$ shear rate.) Each mixture was introduced into the anterior region of the suprachoroidal space at the pars plana in the anterior region of the eye in the manner of Example 1. After 24 hours perfusion, the microspheres in Healon and Healon GV were found to be in process of migration to the posterior region of the suprachoroidal space with the formulation found at both the pars plana site of instillation and the posterior pole. The microspheres in Healon 5 remained dispersed in the viscoelastic localized at the original injection site in the pars plana region of the suprachoroidal space.

Example 4

The experiment of Example 1 was repeated, except that bevacizumab (Avastin™, Genentech) was covalently cross-linked using 1-ethyl-3-(3-dimethylamino propyl)carbodiimide (EDAC, Sigma-Aldrich) onto 5 micron diameter carboxylated fluorescent microspheres and mixed at equal volumes with one of three surgical viscoelastics (Healon, Healon GV, Healon 5, Advanced Medical Optics, Inc.), each with a different viscosity and thixotropic properties as in Example 3. The mixture was introduced into the suprachoroidal space at the pars plana in the manner of Example 1. After 24 hour perfusion the microspheres remained exclusively in the pars plana region of the suprachoroidal space for all viscoelastic carriers.

Example 5

To demonstrate the effect of a crosslinking polymeric excipient on drug localization, the experiment of Example 1 was repeated, except that 10 micron diameter fluorescent microspheres were mixed into a 4% alginate solution and introduced into the suprachoroidal space at the pars plana region. Before sealing the incision site an equal volume of 1 M CaCl2 solution was instilled at the site of the microsphere/alginate suspension to initiate crosslinking of the alginate excipient. The mixture was allowed to gel for 5 minutes before perfusing as in Example 1. The microspheres remained exclusively at the site of instillation, dispersed in the crosslinked polymer excipient.

Example 6

A drug containing injectate was prepared by suspending 1.5 mg of Triamcinolone acetonide in microparticulate form, in 15 microliters of Healon viscoelastic (Advanced Medical Optics, Irvine CA) with a zero shear viscosity of 300,000 mPas and a viscosity of 150 mPas at a shear rate of 1000 s$^{-1}$. Forty porcine subjects were placed under anesthesia and the right eye prepared and draped in a sterile manner. A conjunctival peritomy was made near the superior limbus, exposing and providing surgical access to a region of sclera. A small radial incision was made in the sclera, exposing bare choroid. A flexible microcannula with a 360 micron diameter tip and 325 micron diameter body (iTrack microcannula, iScience Interventional Corp.) was inserted in to the scleral incision and advanced in a posterior direction to a target region behind the macula. The drug suspension was injected into the posterior region of the suprachoroidal space, and was observed to form a layer between the choroid and sclera at the target region. The microcannula was retracted and the scleral and conjunctival incisions closed with 7-0 Vicryl suture. The subjects were observed and eyes tissues recovered at 12 hours, 24 hours, 48 hours, 4 days, 7 days, 14 days, 30 days and 90 days. Angiographic, histologic, and photographic studies of the subjects demonstrated no sign of posterior segment pathology. Recovered samples of choroid demonstrated significant concentration of the drug, in the range of at least 1 mg per gram of tissue at all recovery time periods.

Example 7

A drug-containing formulation comprising 20 mL Healon 5 and 50 mL (1.5 mg) bevacizumab (AvastinTM, Genentech) was prepared. Eighteen porcine subjects were anesthetized and the right eye prepared and draped in a sterile manner. A conjunctival peritomy was made near the superior limbus, exposing and providing surgical access to a region of sclera. A small radial incision was made in the sclera, exposing bare choroid. A flexible microcannula with a 360 micron diameter tip and 325 micron diameter body (iTrack microcannula, iScience Interventional Corp.) was inserted in to the scleral incision and advanced in a posterior direction to a target region behind the macula. The drug formulation was injected into the posterior region of the suprachoroidal space, and was observed to form a layer between the choroid and sclera at the target region. The microcannula was retracted and the scleral and conjunctival incisions closed with 7-0 Vicryl suture. Another 18 porcine subjects were anesthetized and each received a 50 mL bolus of bevacizumab via injection into the vitreous. Both groups of test subjects were evaluated and sacrificed at 0.5, 7, 30, 60, 90, and 120 days post-injection. Serum samples were taken and tested for bevacizumab using an enzyme-based immunoassay. Higher plasma levels of bevacizumab were found in the intravitreally injected subjects and for longer duration of time than the suprachoroidal delivery group. The right globes were removed and dissected in order to quantitate bevacizumab in specific tissues and regions using an enzyme-based immunoassay. The enzyme immunoassay demonstrated that bevacizumab delivered via intravitreal injection was distributed throughout eye, but when delivered suprachoroidally remained largely in the retina and choroid, with little found in the vitreous and anterior chamber.

Example 8

The experiment of Example 1 was repeated, except a drug formulation 0.2 mL of Healon 5, 0.6 mL of Avastin, and 24 mg of triamcinolone acetonide was prepared to provide a treatment with both anti-inflammatory and anti-VEGF properties. An approximately 5 mm long incision was made longitudinally in the pars plana region transecting the sclera, exposing the choroid of a cadaver globe that had been clarified by immersion in glycerol for approximately 30 minutes and perfused with saline at 12 mm Hg pressure. The flexible microcannula of Example 6 was primed with the drug formulation and the microcannula tip was inserted into the suprachoroidal space through the scleral incision. With the aid of the fiber optic beacon at the microcannula tip, the distal end of the microcannula was steered toward the posterior pole of the globe, stopping approximately 5 mm short of the optic nerve. Using a Viscoelastic Injector (iScience Interventional), 70 microliters of the drug formulation was injected into the posterior region of the suprachoroidal space. The microcannula was removed by withdrawing though the pars plana incision. The mixture was visible though the clarified sclera, and formed a deposit near the optic nerve with the mixture also following the catheter track. The incision was sealed with cyanoacrylate (Locktite 4011) and the globe perfused again with saline at 12 mm Hg for 3 hours. The sclera was re-cleared by immersion in glycerol to examine the administered drug formulation. The drug formulation was observed by microscopy to have formed a layer of dispersed drug within the polymer excipient in the posterior region of the suprachoroidal space.

Example 9

A series of experiments were performed to evaluate minimally invasive delivery of substances to the suprachoroidal space. The goal of the experiments was to use non-invasive imaging and fluid dissection as a means of delivering substances through scleral tissue and into the suprachoroidal space, without having direct penetration into the suprachoroidal space.

Human cadaver eyes were obtained from an eye bank and were prepared by inflating the eyes to approximately 20 mm Hg pressure with phosphate buffered saline (PBS). A delivery needle was fabricated using stainless steel hypodermic tubing, 255 mm ID×355mm OD. The needle distal tip was ground into a bi-faceted short bevel point, 400 um in length and at an angle of 50°. The fabricated needle was then silver-soldered into a standard 25 gauge×1 inch hypodermic needle to complete the assembly.

The needle was gently advanced into scleral tissue at an acute angle (<10°) with respect to the surface of the eye. The needle entry was started in the pars plana region approximately 4 mm from the limbus, and the needle advanced posteriorly in scleral tissue to create a tract between 5 and 6 mm long without penetrating through the sclera into the suprachoroidal space. A high resolution ultrasound system (iUltrasound, iScience Surgical Corp.) was used to guide and verify placement of the needle tip within scleral tissues and to document the injections.

In the first set of experiments, a polymeric excipient alone comprising a hyaluronic acid surgical viscoelastic (Healon 5, Advanced Medical Optics, Inc) was injected. In a second set of experiments, the viscoelastic was mixed in a 1:1 ratio with a 1% aqueous solution of 10 micron diameter polystyrene microspheres (Duke Scientific, Inc) to represent a model microparticulate drug. The viscoelastic and the mixture were delivered through the needle using a screw driven syringe (ViscoInjector, iScience Surgical Corp.) in order to control delivery volume and injection pressure. The injections were made with the needle bevel turned inwards towards the center of the globe. Multiple locations on three cadaver eyes were used for the experiments.

Figure 2:
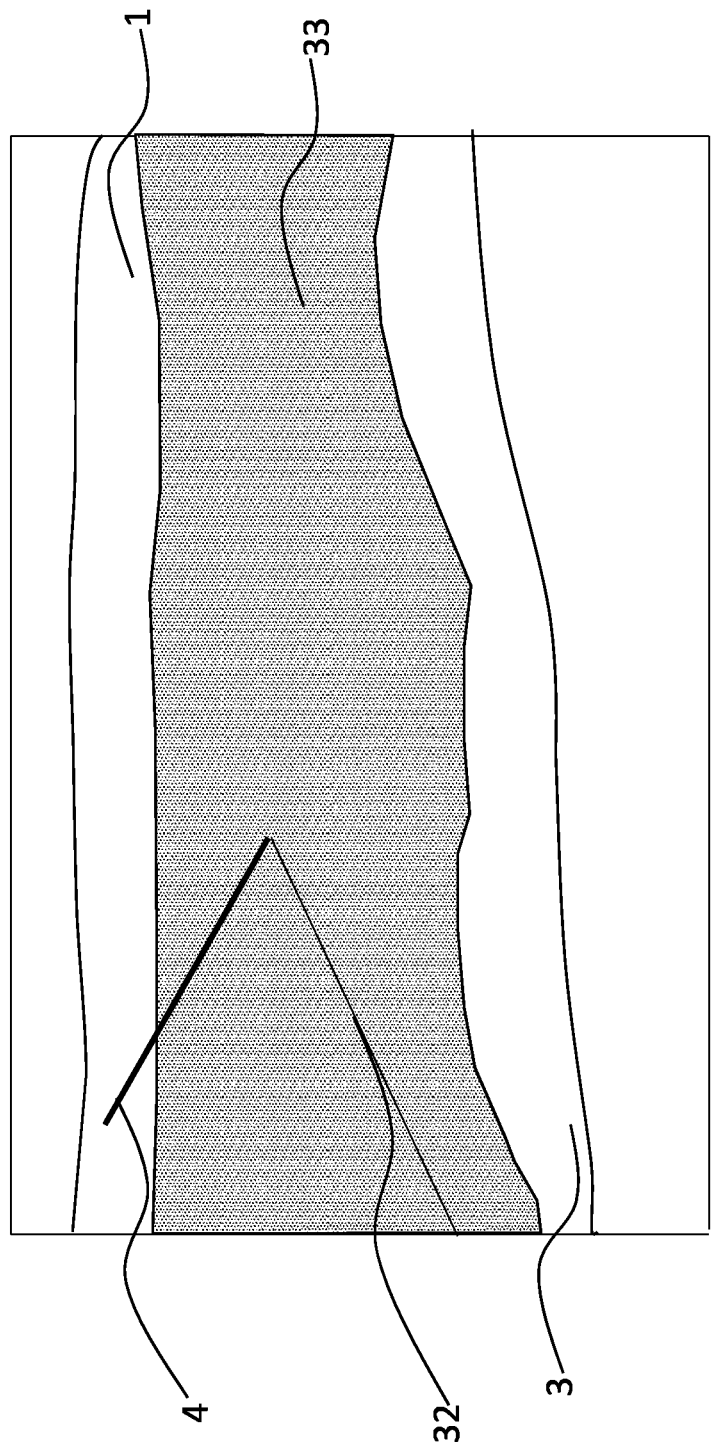
FIG. 2 is an ultrasonic image of a portion of the eye during injection by needle into the sclera of a 1:1 by volume mixture of the viscoelastic material and 1% solution of polystyrene microspheres according to Example 9.

In the first experiments, the needle tract was approximately 3 to 4 mm in length and the injectate was observed to flow back out the tract. With placement of the needle tip in a longer tract, higher injection pressure was obtained and allowed the injectate to dissect through the remaining interposing layers of the sclera and deliver to the suprachoroidal space. Through trials it was found that needle tip placement in the outer layers of the sclera (<1/2 scleral thickness) resulted in the delivery of the viscoelastic into an intrascleral pocket or sometimes through to the outer surface of the globe. With the needle tip approaching the basement of the sclera, the injections dissected through the remaining interposing scleral tissue, entered the suprachoroidal space and spread to fill the suprachoroidal space in the region of the injection. FIG. 1 shows the needle tract 30 clearly visible (after removal of the needle) and a region 31 of the suprachoroidal space filled with injectate. The sclera 1 and choroid 3 are shown. FIG. 2 shows a region 33 of the suprachoroidal space filled with the microsphere and hyaluronic acid excipient containing injectate, and the tip of the needle 4 in the sclera and needle shadow 32.

Example 10

An experiment was performed to use micro-endoscopic imaging to allow minimally invasive access to the suprachoroidal space in a human cadaver eye. A custom fabricated, flexible micro-endoscope (Endoscopy Support Services, Brewster NY) with an outer diameter of 350 microns containing an imaging bundle with 1200 pixels was mounted on a micrometer adjusted stage. The stage was mounted on a vertical stand allowing for controlled up and down travel of the endoscope. The micro-endoscope was attached to a ½" chip CCD camera and then to a video monitor. A 20 gauge hypodermic needle was placed over the endoscope to provide a means for piercing the tissues for access.

The camera was turned on and an external light source with a light pipe (Model MI-150, Dolan Jenner, Boxborough, MA) was used to provide transcleral imaging illumination. The needle was advanced until the distal tip was in contact with the scleral surface of a human cadaver whole globe approximately 4 mm posterior of the limbus. The micro-endoscope was then lowered until the white scleral surface could be seen through the end of the needle. The needle was then slowly advanced into the scleral tissue by slight back-and-forth rotation. As the needle was advanced in this manner, the endoscope was lowered to follow the tract created by the needle. At or within the sclera, the endoscopic image was seen as white or whitish-grey. As the needle pierced the scleral tissues, the image color changed to dark brown indicating the presence of the dark choroidal tissues, demonstrating surgical access of the suprachoroidal space.

Example 11

An experiment was performed to use fiber-optic illuminated guidance to allow minimally invasive access to the suprachoroidal space in a human cadaver eye. A flexible microcannula with an illuminated distal tip (iTrack-250A, iScience Interventional, Menlo Park, CA) was placed into a 25 gauge hypodermic needle. The microcannula comprised a plastic optical fiber that allowed for illumination of the distal tip. The microcatheter fiber connector was attached to a 635 nm (red) laser diode fiber optic illuminator (iLumin, iScience Interventional) and the illuminator turned on to provide a steady red light emanating for the microcannula tip. The microcannula was fed through the 25 gauge needle up to the distal bevel of the needle but not beyond.

The needle was slowly advanced in the pars plana region of a human cadaver whole globe until the needle tip was sufficiently embedded in the scleral tissues to allow a slight advancement of the microcannula. The illumination from the microcannula tip was seen clearly as the scleral tissues diffused the light to a significant extent. As the needle was advanced slowly, the microcannula was pushed forward at the same time. When the hypodermic needle tip pierced through sufficient scleral tissue to reach the suprachoroidal space, the red light of the microcannula tip immediately dimmed as the illuminated tip passed out of the diffusional scleral tissues and into the space beneath. The microcannula was advanced while keeping the needle stationary, thereby placing the microcannula tip into the suprachoroidal space. Further advancement of the microcannula in a posterior direction in the suprachoroidal space could be seen transclerally as a focal red spot without the broad light diffusion seen when the tip was inside the scleral tissues. Using a high frequency ultrasound system (iUltraSound, iScience Interventional), the location of the microcannula in the suprachoroidal space was confirmed.

The invention claimed is:

1. A method, comprising:
    advancing a distal end portion of a puncture member of a medical injector through a sclera of an eye until the distal end portion of the puncture member reaches a suprachoroidal space (SCS), the puncture member defining a lumen having a longitudinal axis;
    moving a flexible cannula distally relative to the puncture member such that an atraumatic distal end of the flexible cannula exits the lumen along the longitudinal axis, and beyond the distal end portion of the puncture member along the SCS, thereby expanding the SCS; and
    administering a drug formulation to the expanded SCS.

2. The method of claim 1, further comprising:
    during the moving, illuminating the SCS via the flexible cannula to verify disposal of the flexible cannula in the SCS.

3. The method of claim 1, wherein prior to the moving, the atraumatic distal end of the flexible cannula is disposed in the lumen of the puncture member proximal to the distal end portion of the puncture member.

4. The method of claim 1, wherein the flexible cannula includes a lubricious coating to aid in advancement of the flexible cannula.

5. The method of claim 1, wherein the puncture member is a needle having a gauge between about 20 to about 25.

6. The method of claim 1, wherein the distal end portion of the puncture member is in-line with a proximal end portion of the puncture member.

7. The method of claim 1, wherein the flexible cannula provides an inward distending action to the choroid upon contacting the choroid to prevent trauma to a choroid.

8. The method of claim 1, further comprising:
guiding placement of the distal end portion of the puncture member via a sensor.

9. The method of claim 8, wherein the sensor includes at least one of a light pipe or an ultrasound sensor.

10. A method of administering a therapeutic substance to an eye via an ocular injector, the ocular injector including a puncture member defining a lumen with a longitudinal axis and a flexible cannula movably disposed in the lumen, the flexible cannula having an atraumatic distal tip, the method comprising:
inserting a distal end portion of the puncture member into the eye until the distal end portion of the puncture member reaches a suprachoroidal space (SCS);
advancing the flexible cannula distally through the lumen of the puncture member such that the atraumatic distal tip of the flexible cannula exits the lumen along the longitudinal axis, thereby expanding the SCS; and
administering the therapeutic substance to the expanded SCS such that the therapeutic substance is advanced posteriorly in the SCS.

11. The method of claim 10, further comprising:
during the advancing, illuminating the SCS via the flexible cannula to verify disposal of the flexible cannula in the SCS.

12. The method of claim 10, wherein the flexible cannula includes a lubricious coating to aid in advancement of the flexible cannula.

13. The method of claim 10, wherein the puncture member is a needle having a gauge between about 20 to about 25.

14. The method of claim 10, wherein the distal end portion of the puncture member is in-line with a proximal end portion of the puncture member.

15. The method of claim 10, wherein the flexible cannula provides an inward distending action to the choroid upon contacting the choroid to prevent trauma to a choroid.

16. A method of administering a drug formulation to an eye via an ocular injector, the ocular injector including a puncture member defining a lumen with a longitudinal axis and a flexible cannula movably disposed in the lumen, the flexible cannula having an atraumatic distal tip, the method comprising:
inserting a distal end portion of the puncture member into the eye until the distal end portion of the puncture member reaches a suprachoroidal space (SCS);
advancing the flexible cannula distally through the lumen of the puncture member such that the atraumatic distal tip of the flexible cannula exits the lumen along the longitudinal axis, thereby expanding the SCS; and
administering the drug formulation to the expanded SCS such that the drug formulation is advanced posteriorly in the SCS.

17. The method of claim 16, further comprising:
during the advancing, illuminating the SCS via the flexible cannula to verify disposal of the flexible cannula in the SCS.

18. The method of claim 16, wherein the flexible cannula includes a lubricious coating to aid in advancement of the flexible cannula.

19. The method of claim 16, wherein the puncture member is a needle having a gauge between about 20 to about 25.

20. The method of claim 16, wherein the distal end portion of the puncture member is in-line with a proximal end portion of the puncture member.

21. The method of claim 16, wherein the flexible cannula provides an inward distending action to the choroid upon contacting the choroid to prevent trauma to a choroid.

22. The method of claim 16, wherein the flexible cannula includes a microcatheter.

\* \* \* \* \*